(12) United States Patent
Anson et al.

(10) Patent No.: US 12,569,843 B2
(45) Date of Patent: Mar. 10, 2026

(54) SYSTEMS AND METHODS FOR WET AIR OXIDATION REGENERATION OF CATALYSTS WITH ION EXCHANGE

(71) Applicants: VIRENT, INC., Madison, WI (US); JOHNSON MATTHEY DAVY TECHNOLOGIES LIMITED, London (GB)

(72) Inventors: Colin Anson, Madison, WI (US); Edgar Steenwinkel, Madison, WI (US); Matt van Straten, Madison, WI (US); Ian Campbell, London (GB)

(73) Assignees: Virent, Inc, Madison, WI (US); Johnson Matthey Davy Technologies Limited, London (GB)

( * ) Notice: Subject to any disclaimer, the term of this patent is extended or adjusted under 35 U.S.C. 154(b) by 197 days.

(21) Appl. No.: 18/582,047

(22) Filed: Feb. 20, 2024

(65) Prior Publication Data

US 2024/0278226 A1     Aug. 22, 2024

Related U.S. Application Data

(60) Provisional application No. 63/485,982, filed on Feb. 20, 2023.

(51) Int. Cl.
*B01J 38/70* (2006.01)
*B01J 23/46* (2006.01)
(Continued)

(52) U.S. Cl.
CPC ............. *B01J 38/70* (2013.01); *B01J 23/462* (2013.01); *B01J 23/96* (2013.01); *B01J 38/02* (2013.01);
(Continued)

(58) Field of Classification Search
CPC . B01J 38/70; B01J 23/462; B01J 23/96; B01J 38/02; B01J 38/12; C07C 1/22;
(Continued)

(56) References Cited

U.S. PATENT DOCUMENTS

| | | |
|---|---|---|
| 3,661,798 A | 5/1972 | Cosyns et al. |
| 4,072,628 A | 2/1978 | Kruse et al. |

(Continued)

FOREIGN PATENT DOCUMENTS

| | | |
|---|---|---|
| EP | 37137 A2 | 10/1981 |
| WO | 2008109877 A1 | 9/2008 |

(Continued)

OTHER PUBLICATIONS

Cao et al., Biomass-derived N-doped porous two-dimensional carbon nanosheets supported ruthenium as effective catalysts for the selective hydrogenation of quinolines under mild conditions, Catalysis Communications, 2020, 143, 5 pages (Year: 2020).
(Continued)

*Primary Examiner* — Ali Z Fadhel
(74) *Attorney, Agent, or Firm* — Quarles & Brady LLP

(57) ABSTRACT

The present disclosure provides systems and methods for regenerating a hydrogenation catalyst with reduced water consumption and/or shortened overall regeneration time. The method can include contacting a fouled hydrogenation catalyst with a first flushing medium comprising water and a gaseous phase comprising oxygen and optionally a second flushing medium comprising water and a gaseous phase comprising at least 90% nitrogen by volume. The method can further include treating the effluents of the flushing mediums by ion exchange resin to remove impurities in the effluents.

20 Claims, 6 Drawing Sheets

(51) Int. Cl.

| | |
|---|---|
| *B01J 23/96* | (2006.01) |
| *B01J 38/02* | (2006.01) |
| *B01J 38/12* | (2006.01) |
| *C07C 1/22* | (2006.01) |
| *C07C 5/02* | (2006.01) |

(52) U.S. Cl.
CPC .................. *B01J 38/12* (2013.01); *C07C 1/22* (2013.01); *C07C 5/02* (2013.01); *C07C 2523/46* (2013.01)

(58) Field of Classification Search
CPC ..... C07C 5/02; C07C 2523/46; C07C 29/132; C10G 2300/1014; C10G 3/47; C10G 3/50
See application file for complete search history.

(56) References Cited

U.S. PATENT DOCUMENTS

| | | | | |
|---|---|---|---|---|
| 4,107,031 | A | * | 8/1978 | Ward ........................ B01J 23/96 208/111.15 |
| 5,217,935 | A | | 6/1993 | Van Driesen |
| 6,300,268 | B1 | | 10/2001 | Lapidus et al. |
| 6,465,529 | B1 | | 10/2002 | Daage et al. |
| 6,566,539 | B1 | | 5/2003 | Campos et al. |
| 6,699,457 | B2 | | 3/2004 | Cortright |
| 6,740,615 | B2 | | 5/2004 | Zhou |
| 6,953,873 | B2 | | 10/2005 | Cortright et al. |
| 6,964,757 | B2 | | 11/2005 | Cortright et al. |
| 6,964,758 | B2 | | 11/2005 | Cortright et al. |
| 7,618,612 | B2 | | 11/2009 | Cortright et al. |
| 7,767,867 | B2 | | 8/2010 | Cortright et al. |
| 7,977,517 | B2 | | 7/2011 | Cortright et al. |
| 7,989,664 | B2 | | 8/2011 | Cortright et al. |
| 8,017,818 | B2 | | 9/2011 | Cortright et al. |
| 8,053,615 | B2 | | 11/2011 | Cortright et al. |
| 8,231,857 | B2 | | 7/2012 | Cortright et al. |
| 8,273,138 | B2 | | 9/2012 | Bauldreay |
| 8,350,108 | B2 | | 1/2013 | Cortright |
| 8,362,307 | B2 | | 1/2013 | Cortright |
| 8,367,882 | B2 | | 2/2013 | Cortright |
| 8,455,705 | B2 | | 6/2013 | Cortright |
| 8,933,281 | B2 | | 1/2015 | Cortright |
| 9,144,797 | B2 | | 9/2015 | Ma |
| 9,427,733 | B2 | | 8/2016 | Co |
| 2006/0111233 | A1 | | 5/2006 | Xiao et al. |
| 2007/0142212 | A1 | * | 6/2007 | Pujado ..................... B01J 29/90 502/34 |
| 2007/0207915 | A1 | * | 9/2007 | Pujado ..................... B01J 38/12 502/34 |
| 2009/0211942 | A1 | | 8/2009 | Cortright et al. |
| 2010/0076233 | A1 | | 3/2010 | Cortright et al. |
| 2010/0248942 | A1 | * | 9/2010 | Xu ........................... B01J 38/34 502/41 |
| 2011/0306804 | A1 | | 12/2011 | Cortright et al. |
| 2015/0126784 | A1 | | 5/2015 | Ma |
| 2016/0332154 | A1 | | 11/2016 | Ma |
| 2020/0016581 | A1 | * | 1/2020 | Gaffney .................. C10G 1/10 |
| 2023/0072588 | A1 | | 3/2023 | Blommel et al. |
| 2024/0246069 | A1 | | 7/2024 | Steenwinkel |
| 2024/0278226 | A1 | | 8/2024 | Anson |

FOREIGN PATENT DOCUMENTS

| | | |
|---|---|---|
| WO | 2011002912 A2 | 1/2011 |
| WO | 2023023290 A1 | 2/2023 |

OTHER PUBLICATIONS

Machine translation of Maisin (EP0037137) publication date May 2, 1984, 9 pages.
Öztürk, Y., & Ekmekçi, Z. (2020). Removal of sulfate ions from process water by ion exchange resins. Minerals Engineering, 159, 106613: 1-11.
Thommes, et al., "Physisorption of gases, with special reference to the evaluation of surface area and pore size distribution (IUPAC Technical Report)", Ppure Appl. Chem. 2015; 87(9-10): 1051-1069.
PCT International Search Report and Written Opinion, PCT/US2022/040820, Dec. 20, 2022, 11 pages.
PCT International Search Report, PCT/US2022/012060, Aug. 1, 2024, 4 pages.
Written Opinion of the International Searching Authority, PCT/US2022/012060, Aug. 1, 2024, 10 pages.
PCT International Search Report, PCT/US2024/016501, Jun. 4, 2024, 5 pages.
Written Opinion of the International Searching Authority, PCT/US2024/016501, Jun. 4, 2024, 9 pages.

* cited by examiner

SYSTEMS AND METHODS FOR WET AIR OXIDATION REGENERATION OF CATALYSTS WITH ION EXCHANGE

CROSS-REFERENCE TO RELATED APPLICATIONS

This application claims priority to U.S. Provisional Application No. 63/485,982, filed Feb. 20, 2023, the content of which is hereby incorporated by reference in its entirety.

BACKGROUND

Biomass is one category of possible renewable alternatives to petroleum-based fuels, chemicals, and other products. However, it remains challenging to develop efficient, cost effective, and environmentally benign technologies for converting biomass to useful products.

As a promising approach, bioreforming processes provide liquid fuels and chemicals derived from the cellulose, hemicellulose and lignin found in plant cell walls. For instance, cellulose and hemicellulose can be used as feedstock for various bioreforming processes, including aqueous phase reforming (APR) and hydrodeoxygenation (HDO)—catalytic reforming processes that, when integrated with hydrogenation, can convert cellulose and hemicellulose into hydrogen and hydrocarbons, including liquid fuels and other chemical products. APR and HDO methods and techniques are described in U.S. Pat. Nos. 6,699,457; 6,964,757; 6,964,758; and 7,618,612 (all to Cortright et al., entitled "Low-Temperature Hydrogen Production from Oxygenated Hydrocarbons"); U.S. Pat. No. 6,953,873 (to Cortright et al., entitled "Low-Temperature Hydrocarbon Production from Oxygenated Hydrocarbons"); and U.S. Pat. Nos. 7,767,867 and 7,989,664 and U.S. Application No. 2011/0306804 (all to Cortright, entitled "Methods and Systems for Generating Polyols"). Various APR and HDO methods and techniques are described in U.S. Pat. Nos. 8,053,615; 8,017,818; 7,977,517; 8,362,307; 8,367,882; 8,455,705; and 8,933,281 (all to Cortright and Blommel, entitled "Synthesis of Liquid Fuels and Chemicals from Oxygenated Hydrocarbons"); U.S. Pat. No. 8,231,857 (to Cortright, and entitled "Catalysts and Methods for Reforming Oxygenated Compounds"); U.S. Pat. No. 8,350,108 (to Cortright et al., entitled "Synthesis of Liquid Fuels from Biomass"); International Patent Application Publication No. WO 2008/109877 (to Cortright and Blommel, entitled "Synthesis of Liquid Fuels and Chemicals from Oxygenated Hydrocarbons"); all of which are incorporated herein by reference.

In certain applications, it may be beneficial for biomass feedstock to be hydrogenated to increase the thermal stability of the biomass feedstock prior to use as a feed for APR and/or HDO. At temperatures compatible with APR and/or HDO, sugars are susceptible to thermal degradation, which leads to byproduct formation, catalyst fouling, and, ultimately, shortened time between catalyst regenerations. This problem is avoided by reacting sugars with hydrogen to form polyols or sugar alcohols that are more thermally stable.

Biomass feedstock includes impurities, such as sulfur-containing moieties, that poison hydrogenation catalysts over time. Poisoning of the catalyst leads to lower conversion and yield of polyol and sugar alcohol products. As a result, most industrial applications involve a batch or semi-continuous process that involves changing the spent catalyst with fresh catalyst or regenerating the existing catalyst to improve conversion. Changing the hydrogenation catalyst frequently is time consuming, expensive, and can lead to production downtime. Significantly, the poisoning or deactivation of the hydrogenation catalyst is worsened where the feedstock includes elevated sulfur-containing impurities.

Current methods for regenerating hydrogenation catalysts include using multiple hydrogen peroxide washes to remove impurities from the spent hydrogenation catalyst. However, hydrogen peroxide damages the physical strength of the catalyst over time, reducing both total surface area and, ultimately, catalytic activity. There remains a need for more effective, less damaging regeneration systems and methods that restore the catalytic capacity of the hydrogenation catalysts under industrial production conditions.

SUMMARY OF THE INVENTION

Described herein are reactor systems and methods for regenerating hydrogenation catalysts for use in hydrogenating feedstock solutions, such as water-soluble sugars derived from biomass and/or unsaturated hydrocarbon streams. The provided reactor systems and methods offer unique features and advantages over existing regeneration technologies. This is an improvement over current technologies to regenerate catalytic activity, such as hydrogen peroxide-based methods, which have a tendency to degrade the catalyst's surface area and pore structure over time. Further, hydrogen peroxide poses storage challenges on a commercial scale. The regenerative oxidants provided herein are cheaper than hydrogen peroxide and can be stored at commercial scale using existing technology.

In one aspect, the present disclosure provides a method for hydrogenating biomass. The method may comprise catalytically reacting a feedstock stream comprising water and an oxygenated hydrocarbon ($C_{2+}O_{1+}$) with hydrogen in the presence of a hydrogenation catalyst for a hydrogenation duration to produce a first hydrogenated product stream and a fouled hydrogenation catalyst. The method may further comprise subjecting the fouled hydrogenation catalyst to a regeneration cycle to produce a regenerated hydrogenation catalyst. The regeneration cycle can include: (a-i) contacting the catalyst with a first flushing medium for an air-treatment duration to produce an air-treated catalyst and a first effluent, wherein the first flushing medium comprises, measured at 25° C. and 1 atmospheric pressure, liquid water and a gaseous phase comprising oxygen; (b) contacting at least a portion of the first effluent with an ion exchange resin to produce a first IX-treated effluent; and (c) recycling the first IX-treated effluent to step (a-i) for inclusion in the first flushing medium. The method may further comprise catalytically reacting the feedstock stream with hydrogen in the presence of the regenerated hydrogenation catalyst to further produce a second hydrogenated product stream. In some embodiments, the regeneration cycle can further include (a-ii) contacting the air-treated catalyst with a second flushing medium for a nitrogen-treatment duration to produce a nitrogen-treated catalyst and a second effluent, wherein the second flushing medium comprises, measured at 25° C. and 1 atmospheric pressure, liquid water and a gaseous phase comprising at least 90% nitrogen by volume; (b) contacting at least a portion of the first effluent and at least a portion of the second effluent with the ion exchange resin to produce the first IX-treated effluent and a second IX-treated effluent, respectively, and (c) recycling the first IX-treated effluent and the second IX-treated effluent to steps (a-i) and (a-ii) for inclusion in the first flushing medium and the second flushing medium, respectively.

In another aspect, the present disclosure provides a method for producing a regenerated hydrogenation catalyst from a fouled hydrogenation catalyst. The method may comprise catalytically reacting a feedstock stream having at least one sulfur-containing impurity in the presence of a hydrogenation catalyst to produce the fouled hydrogenation catalyst, wherein the fouled hydrogenation catalyst comprises an amount of sulfur derived from the at least one sulfur-containing impurity of the feedstock stream. The method may further comprise subjecting the fouled hydrogenation catalyst to a regeneration cycle to produce the regenerated hydrogenation catalyst. The regeneration cycle can include: (a-i) contacting the catalyst with a first flushing medium for an air-treatment duration to produce an air-treated catalyst and a first effluent, wherein the first flushing medium comprises, measured at 25° C. and 1 atmospheric pressure, liquid water and a gaseous phase comprising oxygen; (b) contacting at least a portion of the first effluent with an anionic ion exchange resin to produce a first IX-treated effluent; and; (c) recycling the first IX-treated effluent to step (a-i) for inclusion in the first flushing medium. In particular, the amount of sulfur in the regenerated hydrogenation catalyst is reduced relative to the fouled hydrogenation catalyst. In some embodiments, the regeneration cycle can further comprise: (a-ii) contacting the air-treated catalyst with a second flushing medium for a nitrogen-treatment duration to produce a nitrogen-treated catalyst and a second effluent, wherein the second flushing medium comprises, measured at 25° C. and 1 atmospheric pressure, liquid water and a gaseous phase comprising at least 90% nitrogen by volume; (b) contacting at least a portion of the first effluent and at least a portion of the second effluent with the ion exchange resin to produce the first IX-treated effluent and a second IX-treated effluent, respectively, and (c) recycling the first IX-treated effluent and the second IX-treated effluent to steps (a-i) and (a-ii) for inclusion in the first flushing medium or the second flushing medium, respectively.

In some embodiments, the present method comprises subjecting the fouled hydrogenation catalyst to multiple regeneration cycles. The conditions of one regeneration cycle (such as temperature, pressure, and duration) may be controlled independent of the corresponding conditions of another regeneration cycle. In some embodiments, each of the multiple regeneration cycles can independently include step (a-i), (b), and (c); or steps (a-i), (a-ii), (b) and (c).

In various embodiments, the hydrogenation catalysts of the present methods may include ruthenium on carbon (Ru/C).

DETAILED DESCRIPTION OF THE INVENTION

Described herein are reactor systems and methods for regenerating hydrogenation catalysts for use in hydrogenating feedstock solutions, such as water-soluble sugars derived from biomass and/or unsaturated hydrocarbon streams. The provided reactor systems and methods offer unique features and advantages over existing regeneration techniques.

A wet air oxidation regeneration (WAOR) system was disclosed in the co-pending U.S. patent application Ser. No. 17/891,093 ("SYSTEMS AND METHODS FOR WET AIR OXIDATION REGENERATION OF CATALYSTS," filed Aug. 18, 2022), the content of which is incorporated herein by reference in its entirety. The WAOR system offers mild reaction conditions that can effectively remove impurities to restore hydrogenation catalytic activity, while additionally maintaining the catalyst's structural integrity (e.g., surface area, pore volume). Maintaining the catalyst's structural integrity and/or catalytic activity for extended periods of time improves operation economics by reducing the number of times the catalyst needs to be replaced over time and/or reducing the required frequency of regeneration operations.

A pulsed wet air oxidation regeneration (pulsed WAOR) system capable of atmospheric switching between oxidative (e.g., air) and inert (e.g., nitrogen) flushing media was disclosed in the co-pending U.S. patent application Ser. No. 18/416,818 ("SYSTEMS AND METHODS FOR WET AIR OXIDATION REGENERATION OF CATALYSTS WITH ATMOSPHERIC SWITCHING," filed Jan. 18, 2024), the content of which is incorporated herein by reference in its entirety. The pulsed WAOR can offer more efficient regeneration results as well as the additional advantage of effectively regenerating catalysts used in hydrogenating feedstocks with a high level of sulfur-containing impurities.

In practice, both WAOR and pulsed WAOR processes can be used for the regeneration of Ru/C-based catalysts in the hydrogenation of biomass (e.g., corn syrup) feeds. While these processes are effective at recovering catalyst activity, there are some process-based characteristics that are undesirable. These characteristics are the tradeoff between 1) the amount of fresh water consumption needed to flush the system and 2) the overall time the regeneration process needs. To shorten the overall regeneration time, rinse water can be flowed in a once-through manner, but this produces significant quantities of wastewater that needs to be disposed of or processed. On the other hand, an aqueous recycle can be used to minimize fresh water consumption, but significantly longer rinse times are then needed to remove all of the sulfate from the system, which is produced during catalyst regeneration.

Figure 1A:
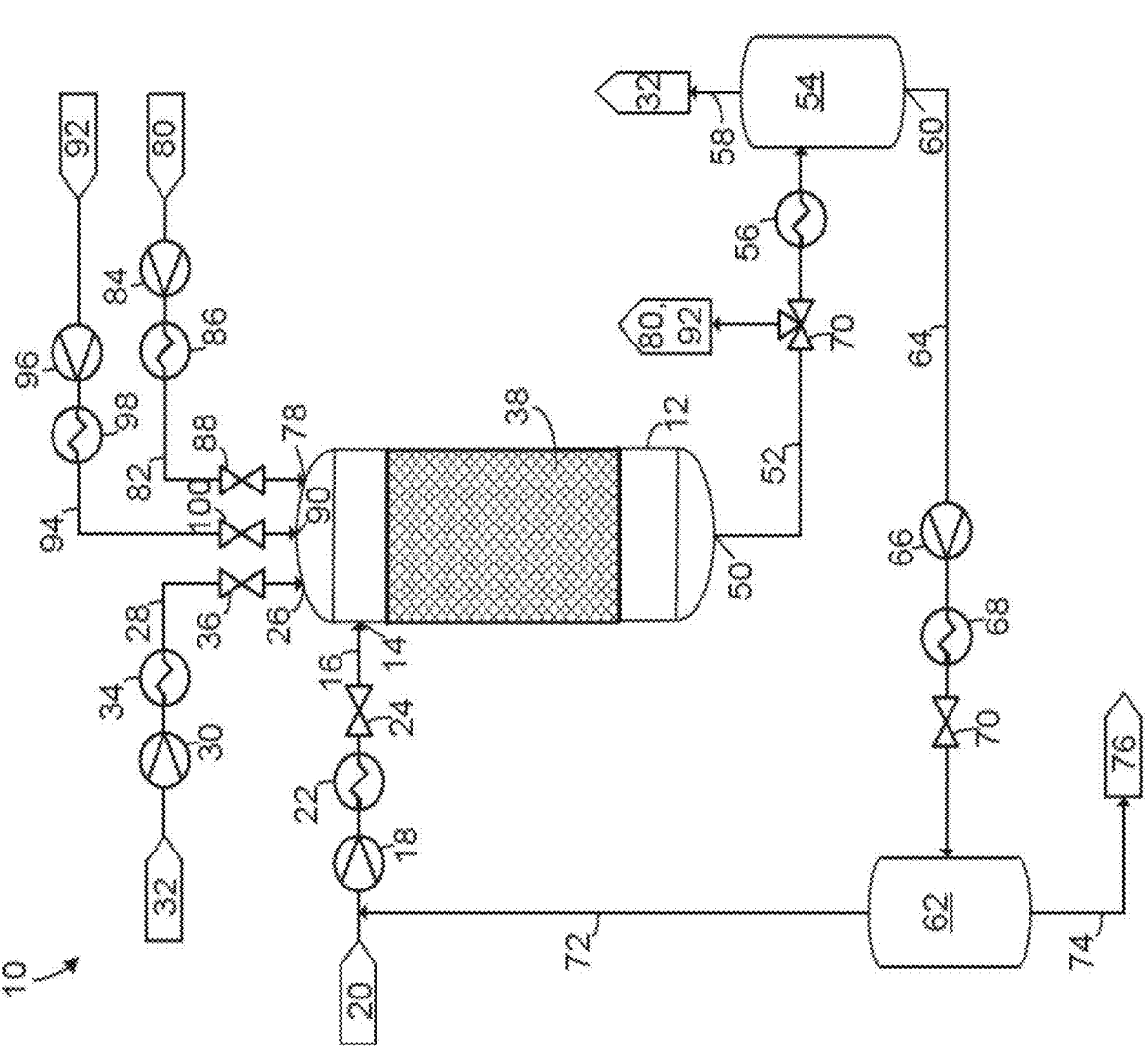
FIG. 1A shows an example reactor system in accordance with some embodiments of the present disclosure.
Figure 1B:
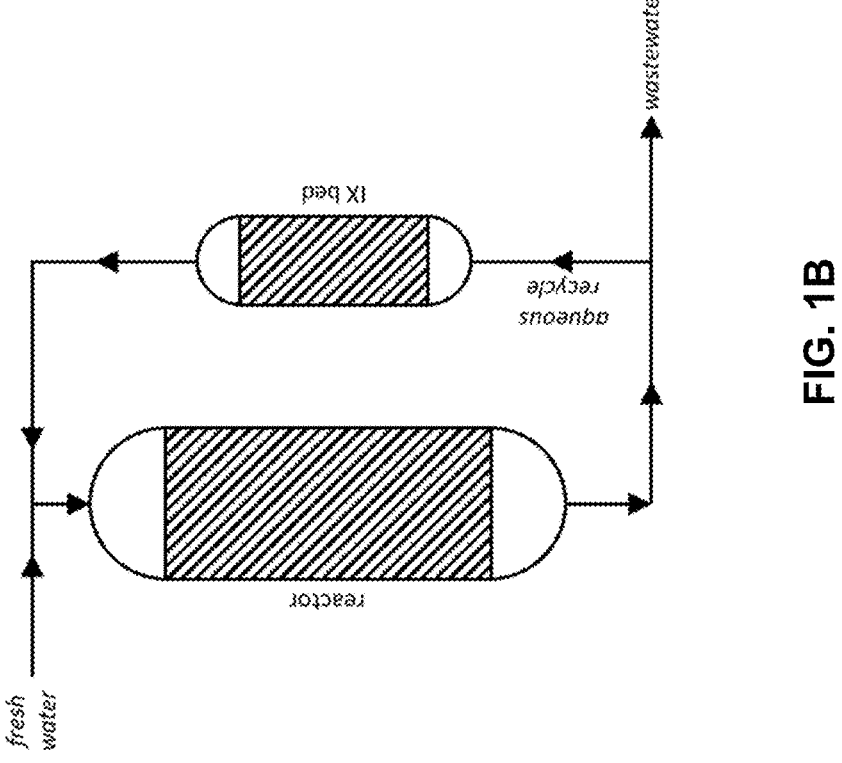
FIG. 1B shows a schematic illustration of a catalyst reactor equipped with an ion exchange unit (IX bed) as disclosed herein. While a nonlimiting exemplary implementation is shown in FIG. 1B, the ion exchange unit can be connected to the catalyst reactor in various other configurations, all of which are contemplated by the present disclosure.

The present disclosure includes distinct features and improves the processes disclosed in standard WAOR and pulsed WAOR methods. In various non-limiting embodiments, to take advantage of shorter regeneration times without significant increases in fresh water usage, the present disclosure provides a system incorporating an ion exchange (IX) bed in the recycle line to remove impurities (e.g., sulfate) from the regeneration flow. For example, in a pulsed WAOR process, the present system and method allow short $N_2$/air cycles. In particular embodiments, an IX bed containing anion exchange resin can be configured to process the effluent of a hydrogenation reactor to remove sulfate in the effluent and recycle the IX-treated effluent back to the reactor (FIG. 1B).

In one aspect, the present disclosure provides a method for hydrogenating biomass, the method comprising:

catalytically reacting a feedstock stream comprising water and an oxygenated hydrocarbon ($C_{2+}O_{1+}$) with hydrogen in the presence of a hydrogenation catalyst for a hydrogenation duration to produce a first hydrogenated product stream and a fouled hydrogenation catalyst;

subjecting the fouled hydrogenation catalyst to a regeneration cycle to produce a regenerated hydrogenation catalyst, the regeneration cycle comprising:

(a-i) contacting the catalyst with a first flushing medium for an air-treatment duration to produce an air-treated catalyst and a first effluent, wherein the first flushing medium comprises, measured at 25° C. and 1 atmospheric pressure, liquid water and a gaseous phase comprising oxygen;

(b) contacting at least a portion of the first effluent with an ion exchange resin to produce a first IX-treated effluent; and (c) recycling the first IX-treated effluent to step (a-i) for inclusion in the first flushing medium, and catalytically reacting the feedstock stream with hydrogen in the presence of the regenerated hydrogenation catalyst to further produce a second hydrogenated product stream.

In some embodiments, the regeneration cycle of the present method further comprises:

(a-ii) contacting the air-treated catalyst with a second flushing medium for a nitrogen-treatment duration to produce a nitrogen-treated catalyst and a second effluent, wherein the second flushing medium comprises, measured at 25° C. and 1 atmospheric pressure, liquid water and a gaseous phase comprising at least 90% nitrogen by volume;

(b) contacting at least a portion of the first effluent and at least a portion of the second effluent with the ion exchange resin to produce the first IX-treated effluent and a second IX-treated effluent, respectively, and (c) recycling the first IX-treated effluent and the second IX-treated effluent to steps (a-i) and (a-ii) for inclusion in the first flushing medium and the second flushing medium, respectively.

The present method may be carried out in a reactor system. Referring to FIG. 1A, a representative reactor system 10 is illustrated in accordance to some embodiments of the present disclosure. Although the principles disclosed herein can be beneficially implemented on the illustrated reactor system 10, use of other reactor system architectures is possible for some embodiments. In particular, the reactor system 10 includes a reactor 12 having a feedstock inlet 14 that places the reactor 12 in fluid communication with a feedstock conduit 16. A pump 18 may be configured in the feedstock conduit 16 to transport a feedstock solution from a feedstock source 20, such as a reservoir or upstream process unit, to the reactor 12. The feedstock conduit 16 may include a heat exchanger 22 for controlling the temperature of the feedstock solution, and a valve 24 for controlling the flow of the feedstock solution to the reactor 12.

In some embodiments, suitable feedstock solutions include water-soluble sugars derived from biomass, although other feedstocks can be used. As used herein, the term "biomass" refers to, without limitation, organic materials produced by plants (such as leaves, roots, seeds and stalks), and microbial and animal metabolic wastes. Common biomass sources include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, switch grass, alfalfa, prairie bluestream, corn, soybean, and the like. The feedstock can be fabricated from biomass by any means now known or developed in the future, or can be simply byproducts of other processes. The sugars can also be derived from wheat, corn, sugar beets, sugar cane, or molasses. The sugar is combined with water to provide an aqueous feedstock solution having a concentration effective for hydrogenating the sugar. Generally, a suitable sugar concentration is in the range of about 5% to about 70%, with a range of about 40% to 70% more common in industrial applications.

Additionally or alternatively, suitable feedstock solutions include, but are not limited to, oxygenated hydrocarbons ($C_{2+}O_{1+}$, e.g. cyclic ethers, esters, ketones, lactones, carboxylic acids), vegetable oils (e.g., polyunsaturated fatty acids), olefins (e.g., alkenes and aromatics, such as $C_3$-$C_{12}$ olefins), alkynes, aldehydes, imines, nitriles, thiols, disulfides, thioesters, thioethers, phenols, other arenes/aromatic compounds, and combinations thereof. In some embodiments, the feedstock stream comprising water and an oxygenated hydrocarbon ($C_{2+}O_{1+}$). In some embodiments, the oxygenated hydrocarbon is a saccharide.

Referring back to FIG. 1A, the reactor 12 includes a hydrogen inlet 26 that places the reactor 12 in fluid communication with a hydrogen conduit 28. A gas transport device 30 may be configured in the hydrogen conduit 28 to transport hydrogen from hydrogen source 32, such as a reservoir or upstream process unit, to the reactor 12. In some embodiments, the hydrogen conduit 28 includes a heat exchanger 34 configured to control the heat of the hydrogen stream. Suitable gas transport devices 30 include, but are not limited to, compressors or blowers. Although the hydrogen inlet 26 and the feedstock inlet 14 are orientated in a co-current direction in FIG. 1A, it is to be appreciated that the hydrogen inlet 26 could be arranged in a countercurrent orientation (i.e., fed into the bottom of the reactor 12). The hydrogen conduit 28 may include a valve 36 for controlling the flow of the hydrogen to the reactor 12. Although not illustrated in FIG. 1A, the feedstock and hydrogen may be blended, mixed, or otherwise combined in a mixer prior to being delivered to the reactor 12.

In some embodiments, the reactor 12 includes a hydrogenation catalyst 38 disposed therein. Hydrogenation reactions can be carried out in any reactor of suitable design, including continuous-flow, batch, semi-batch or multi-system reactors, without limitation as to design, size, geometry, flow rates, etc. The reactor system 10 can also use a fluidized catalytic bed system, a swing bed system, a fixed bed system, a moving bed system, or a combination of the above. Reactions of the present disclosure are typically practiced using a continuous flow system at steady-state equilibrium.

In some embodiments, the reactor system 10 operates as a fixed, trickle bed reactor with shell-and-tube heat exchange in which the hydrogen and feedstock solution are introduced at the top of the reactor 12 and allowed to flow downward over a fixed bed of the hydrogenation catalyst 38. The advantages of the trickle bed reactor include a simple mechanical design, a simplified operation and potentially a simplified catalyst development. The main design challenges are ensuring that the heat and mass transfer requirements of the reaction are met. The main operational challenges for trickle bed reactors are: uniformly loading the hydrogenation catalyst 38, uniformly introducing the gas and liquid feeds, and avoiding bypassing of some of the hydrogenation catalyst 38 due to channeling of the reactants as they flow through the reactor 12.

In some embodiments, the reactor system 10 operates as a slurry reactor. While a trickle bed reactor is loaded with an immobile hydrogenation catalyst 38, a slurry reactor contains a flowing mixture of reactants, products, and hydrogenation catalyst 38 particles. Keeping a uniform mixture throughout the reactor 12 includes active mixing either from a mixer or a pump. In addition, to withdraw product the catalyst particles must be separated from the product and unreacted feed by filtration, settling, centrifuging or some other means. The advantages of a slurry reactor are mainly that the active mixing might enable higher heat and mass transfer rates per unit of reactor volume.

In some embodiments, the feedstock solution and the hydrogen are reacted across the hydrogenation catalyst 38 in the reactor 12. In some embodiments, the heat exchangers 22, 34 heat the feedstock solution and hydrogen streams to a temperature from 5° C. to 700° C., from 10° C. to 500° C., from 20° C. to 300° C., or from 50° C. to 180° C. In some embodiments, the pressure of the reactor 12 is maintained from 0 psig to 5000 psig, or from 100 psig to 3000 psig. The hydrogenation catalyst 38 may be configured in the reactor 12 in various configurations including, but not limited to, a single fixed bed or in a shell and tube arrangement. In some embodiments, the reactor system 10 includes a heating system configured to provide heat to the reactor 12 to maintain a desired operating temperature. In some embodiments, the heating system provides heat to the reactor 12 using, for example, a heating element (e.g., electric heaters), a heating fluid, or combinations thereof. The heating system may be configured on the outside of the reactor. Additionally or alternatively, the heating system may be configured in a shell-and-tube configuration, where a heating fluid provides heat to the hydrogenation catalyst 38 via the shell or tube side. In some embodiments, the reactor 12 temperature can also be controlled by recycling the products of the reaction back through the reactor 12 to decrease the reaction exotherms.

The product stream exits the reactor 12 through at least one reactor outlet 50 and is optionally transported to a separator 54 via a product conduit 52. In some embodiments, the product conduit 52 includes a heat exchanger 56 to adjust the temperature of the product stream prior to entering the separator 54. The separator 54 may optionally separate unreacted hydrogen from unreacted reactants and products. The unreacted hydrogen may be recycled to the hydrogen source 32 via a hydrogen recycle conduit 58. Any suitable separator 54 may be used to separate the hydrogen from the unreacted reactants and products, including but not limited to, a settling tank, flash tank, distillation, or a combination thereof. Although not illustrated in FIG. 1A, in some embodiments the reactor 12 may include a gas outlet and a liquid outlet, where the disengagement of vapor and liquid products occurs inside the reactor 12 without the separator 54.

In some embodiments, the separator 54 includes a product outlet 60 that places the separator 54 in fluid communication with a second separator 62 via conduit 64. A pump 66 may transport the product stream and unreacted reactants to the second separator 62. A heat exchanger 68 may control the temperature of the product stream and unreacted reactants entering the second separator 62, and a valve 70 may regulate the flow.

In some embodiments, the second separator 62 is configured to separate the product stream from unreacted reactants. The unreacted reactants may be recycled to the feedstock conduit 16 via recycle conduit 72, or otherwise discarded from the process. The product stream exiting the separator 62 via product conduit 74 may be sent to storage or to downstream processing units 76, such as aqueous phase reforming (APR) or hydrodeoxygenation (HDO) systems. Any suitable separator 62 may be used to separate the product stream from the unreacted reactants, including but not limited to, distillation, evaporation, liquid-liquid extraction, chromatography, or combinations thereof.

Catalyst

The present method may be used for regenerating hydrogenation catalysts, e.g., those used in the hydrogenation of biomass. In some embodiments, suitable hydrogenation catalysts 38 for the reactor system 10 includes hydrogenation catalysts 38 having an active metal and a support. Suitable active metals include, but are not limited to, Fe, Ru, Co, Pt, Pd, Ni, Re, Cu, alloys thereof, and a combination thereof, either alone or with promoters such as Ag, Au, Cr, Zn, Mn, Mg, Ca, Cr, Sn, Bi, Mo, W, B, P, and alloys or combinations thereof.

The hydrogenation catalyst may also include any one of several supports, depending on the desired functionality of the catalyst. Exemplary supports include transition metal oxides, an oxide formed from one or more metalloid, and reactive nonmetals (e.g., carbon). Non-limiting examples of supports include, but are not limited to, carbon, silica, alumina, zirconia, titania, vanadia, ceria, silica-aluminate, zeolite, kieselguhr, hydroxyapatite, zinc oxide, chromia, and mixtures thereof.

In some embodiments, the catalyst is a ruthenium on carbon (Ru/C) hydrogenation catalyst. In some embodiments, the catalyst comprises about 0.1% to about 5% by weight ruthenium loaded onto a carbon particle, which includes, but is not limited to, about 0.5%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, and 4.5% by weight. In some embodiments, the catalyst comprises about 0.1% to about 4.0% or about 1.0% to about 2.0% by weight ruthenium on carbon. The catalyst may be in a form of extrudate, tablet, sphere, granule, powder, foam, a coated structure, or a combination thereof.

The catalyst may be deactivated during the reaction or chemical process it catalyzes. For example, a hydrogenation catalyst as described herein may be deactivated during biomass hydrogenation process. The catalyst may have a surface with active sites, which may affect the capacity of the catalyst in catalyzing the hydrogenation reaction. The catalyst may be deactivated due to various reasons during the hydrogenation process, including, for example, blocking of active sites by physical absorption (or deposition) of bulky molecules, poisoning of active sites by impurities in the feedstock, or a combination thereof. Catalyst poisoning may be caused by, for example, a chemical reaction or strong interaction of the impurities (e.g., sulfur containing compounds) with the active site of the catalyst, thereby lowering the capacity of the catalyst to catalyze the hydrogenation reaction, i.e., thereby deactivating the catalyst. The degree of deactivation of the catalyst may increase over time as the hydrogenation process continues. Although the amounts of impurities in the feedstock may be relatively low, at large volumes and over time the impurities can build up and adversely affect catalyst activity.

A "fresh" catalyst is used to mean a catalyst that has not been exposed to a feedstock solution or the impurities from the feedstock under hydrogenation conditions.

A "fouled hydrogenation catalyst" or "fouled catalyst" as used herein refers to a hydrogenation catalyst in which the active sites are at least partially deactivated due to being used in a hydrogenation process (i.e., exposed to a feedstock solution under conditions for hydrogenation of the feedstock solution using the catalyst). The degree of fouling may be affected, for example, by the composition of the catalyst, the duration and conditions of the hydrogenation process, the composition of the feedstock, and the amounts of impurities in the feedstock.

A "regenerated hydrogenation catalyst" or "regenerated catalyst" as used herein refers to a fouled catalyst whose catalytic capacity is at least partially restored, for example, by removing the deposits and/or accumulated impurities from the catalyst surface, restoring access to active sites, restoring poisoned active sites, or a combination thereof. As described herein, a regenerated catalyst may be re-used in a hydrogenation process and become a fouled catalyst again during the process. In this situation, the regenerated catalyst can also be referred to as a "freshly regenerated" catalyst relative to the fouled catalyst produced from such regenerated catalyst.

The catalytic capacity of a regenerated catalyst, or the catalytic capacity of a fouled catalyst from which the regenerated catalyst is produced, may be compared to that of a fresh catalyst. For example, the catalytic capacity of a fouled catalyst may be about 20%, about 30%, about 40%, about 50%, about 60%, about 70%, about 80%, or about 90% of the catalytic capacity of a fresh catalyst. For example, the catalytic capacity of a regenerated catalyst may be about 80%, about 90%, about 95%, about 99%, about 100%, or about 110% the catalytic capacity of a fresh catalyst. In some embodiments, the regenerated catalyst has more catalytic capacity than the fouled catalyst from which the regenerated catalyst is produced. For example, the regeneration method herein may restore at least a portion of the catalytic capacity in a fouled catalyst, resulting in an increase of the catalytic capacity in the regenerated catalyst. In some embodiments, the catalytic capacity in a regenerated catalyst may be about 105% to about 500% of the catalytic capacity of the fouled catalyst from which the regenerated catalyst is produced, including about 120%, about 150%, about 200%, about 300%, about 400%, or about 500%.

The catalytic capacity of a catalyst (e.g., a fresh, fouled, or regenerated catalyst) can be measured by a conversion rate of a reagent in the feedstock in a reaction (e.g., a hydrogenation reaction) that is catalyzed by such catalyst. As used herein, the term "conversion" of a hydrogenation catalyst refers to the hydrogenation catalyst's conversion over a duration (e.g., at least 1 hour to at least one day) of a reactant in the feedstock solution after being exposed to the feedstock solution for a hydrogenation cycle. The hydrogenation catalyst may be a fresh catalyst, a fouled catalyst, or a regenerated catalyst. As used herein, conversion of a specific feedstock reactant ($X_i$) may be calculated by:

$$X_i = 1 - \frac{n_i(t)}{n_i(t=0)}$$

where $n_i$ is the number of moles of the specific feedstock reactant (e.g., sugar, olefin, vegetable oil, alkyne, aldehyde, imine, nitrile) at the beginning (t=0) or after a specific duration (t) of the hydrogenation process. The conversion values of a fresh catalyst, a fouled catalyst, and a regenerated catalyst may be compared under the same hydrogenation conditions (e.g., at a temperature from 50° C. to 180° C. and a pressure from 100 psig to 3000 psig), as conversion may be a function of temperature and pressure.

In some embodiments, the reactor system 10 includes pre-treatment units or steps to process the feedstock solution and/or hydrogenation catalyst 38. For example, the hydrogenation catalyst 38 may be reduced into an active state. For example, during production, the catalyst can be reduced and, in certain applications, then passivated with low levels of oxygen to stabilize the catalyst when exposed to air. The purpose of the reduction step is to transform any oxidized catalyst into a fully reduced state. For certain feedstock solutions, a pre-treatment step may be included upstream of the reactor system 10. For example, sugars containing glycosidic bonds (e.g., sucrose) may be hydrolyzed prior to hydrogenation in the reactor 12.

Catalyst Regeneration

During hydrogenation, catalyst impurities may build up on the surface of the hydrogenation catalyst 38 and reduce catalytic performance. As used herein, the terms "catalyst impurity" or "impurity" refers to impurities that form deposits that accumulate on catalytic sites on the surface of hydrogenation catalyst 38, restrict access to the catalytic sites, and/or reduce catalytic activity over time (i.e., results in lower conversion and yields of products). Exemplary catalyst impurities include, but are not limited to, carbon-containing impurities, sulfur-containing impurities, silicon-containing impurities, phosphorus-containing impurities, or iron-containing impurities.

In some embodiments, the hydrogenation catalyst 38 is regenerated into a regenerated catalyst by contacting the hydrogenation catalyst 38 with a flushing medium. In some embodiments, the flushing medium comprises a vapor or gaseous phase and a liquid phase. Unless otherwise specified, the terms "vapor phase" and "gaseous phase" are used interchangeably herein with regard to the flushing medium, and the physical properties of the "gaseous phase" and "liquid phase" of the flushing medium are understood to be measured at 25° C. and 1 atmospheric pressure. For example, the flushing medium can include, measured at 25° C. and 1 atmospheric pressure, water as the liquid phase and air or nitrogen in the gaseous phase.

Still referring to FIG. 1A, the reactor 12 includes a vapor phase inlet 78 that places the reactor 12 in fluid communication with a vapor phase source 80 via vapor phase conduit 82. A fluid transport device 84 (e.g., compressor or blower) may be configured in the vapor phase conduit 82 to transport the vapor phase from the vapor phase source 80 to the reactor 12. The vapor phase conduit 82 may include a heat exchanger 86 for controlling the temperature of the flushing medium's vapor phase, and a valve 88 for controlling the flow of the vapor phase to the reactor 12. In some embodiments, the fluid transport device 84 is configured for direct air or atmospheric capture, where the fluid transport device 84 is in fluid communication or in direct fluid communication with atmospheric air for compression. Using air as the vapor phase in the flushing medium offers various advantages. Specifically, this would avoid having to purchase and store other oxidants (e.g., hydrogen peroxide) on site. In some embodiments, the vapor phase source 80 includes a gaseous phase that comprises oxygen, for example, at about 0.1% to about 30% by volume. In some embodiments, the vapor phase source 80 includes an inert gas (e.g., nitrogen, argon, helium, neon, krypton, xenon, radon, or combinations thereof) source and oxygen source (e.g., compressed tank) that may be used to alter the $O_2$ and/or inert gas content of the vapor phase to the concentrations described herein. In some embodiments, the vapor phase source 80 includes at least 50% air by volume, such as at least 60%, at least 70%, at least 80%, at least 90%, at least 95%, at least 96%, at least 97%, at least 98%, or at least 99% air by volume. In some embodiments, the vapor phase source 80 includes at least 90% nitrogen by volume, such as at least 95%, at least 96%, at least 97%, at least 98%, or at least 99% nitrogen by volume. By adjusting the types of gases (e.g., air or inert gases) supplied via vapor phase source 80, the oxidative atmosphere of the flushing medium (e.g., as measured by the amount of oxygen in the gaseous phase) can be tailored.

In some embodiments, the reactor 12 includes a liquid phase inlet 90 that places the reactor 12 in fluid communication with a liquid phase source 92 via liquid phase conduit 94. In some embodiments, the liquid phase comprises water. A pump 96 may be configured in the liquid phase conduit 94 to transport the liquid phase from the liquid phase source 92 to the reactor 12. The liquid phase conduit 94 may include a heat exchanger 98 for controlling the temperature of the flushing medium's liquid phase, and a valve 100 for controlling the flow of the vapor phase to the reactor 12. Although not illustrated in FIG. 1A, the liquid phase and vapor phase may be blended, mixed, or otherwise combined in a mixer prior to being delivered to the reactor 12.

In some embodiments, the regenerated hydrogenation catalyst may be produced by maintaining contact of the flushing medium with the hydrogenation catalyst 38 at a regeneration temperature, a regeneration pressure, and a duration sufficient to remove at least a portion of the impurities from the hydrogenation catalyst 38. Contacting the flushing medium to the hydrogenation catalyst 38 may occur in any suitable flow scheme, including continuous flow of flushing medium over the hydrogenation catalyst 38 without recycle, continuous flow of flushing medium over the hydrogenation catalyst 38 with some or full recycle, batch, or semi-batch flow. In some embodiments, the flushing medium exits the reactor 12 through reactor outlet 50, and is recycled to the flushing medium sources 80, 92 or reactor inlets 78, 90 by controlling the flow in product conduit 52 with valve 102. The liquid phase (e.g., water) and gaseous phase (e.g., air or nitrogen) of the flushing medium may be recycled several times before being replaced by fresh flushing medium. A "recycle rate" refers to ratio of recycled material (e.g., water) to fresh material. The present system can allow a high recycle rate (e.g., 6, 7, 8, 9, or 10) using water as the liquid phase of the flushing medium (e.g.; a recycle rate of 10 corresponds to 10 equivalents of water being recycled per one equivalent of fresh water being introduced to the system). The high recycle rate can reduce water consumption, which is particularly advantageous on large production scales.

The present system and method can be implemented in all previous WAOR processes. As nonlimiting examples, step (a-i) of the present method, which includes the use of a first flushing medium to produce an air-treated catalyst and a first effluent, can be employed to implement a WAOR process as described in U.S. patent application Ser. No. 17/891,093. On the other hand, step (a-ii) of the present method, which includes the use of a second flushing medium to produce a nitrogen-treated catalyst and a second effluent, can be employed in combination with step (a-i) to implement a pulsed WAOR process as described in U.S. patent application Ser. No. 18/416,818.

The effluents contain at least a portion of the water of the first or second flushing medium. The effluents can be free of the gaseous phase of the first or second flushing medium. The effluents can contain at least a portion of the gaseous phase of the first or second flushing medium.

The present regeneration method further includes contacting at least a portion of the effluent with an ion exchange resin to produce an ion exchange-treated (IX-treated) effluent and recycling the IX-treated effluent to the fouled catalyst for inclusion in the flushing medium. Here, the phrase "inclusion in the flushing medium" means that the recycled effluent is mixed with fresh flushing medium that has not contacted the catalyst, fresh water, fresh gaseous phase of the flushing medium that has not contacted the catalyst, or a combination thereof to form a mixture, which is then used as the flushing medium to contact the catalyst.

In some embodiments, the recycled first or second effluent is mixed with water to form a mixture, which is then used as the first or second flushing medium, respectively. In some embodiments, water in the first or second flushing medium is recycled as the first or second effluent (also referred to herein as "aqueous recycle"). The recycled water can then be treated with an ion exchange unit and the treated water can be mixed with fresh water, thereby being included in the flushing medium for re-introduction to the catalyst. FIG. 1B shows a schematic illustration for the aqueous recycle process and mixing of IX treated water with fresh water.

In some embodiments, the recycled first or second effluent is mixed with water and a fresh gaseous phase to form a mixture, which is then used as the first or second flushing medium, respectively.

Regeneration Cycle

In some embodiments, the first flushing medium comprises, measured at 25° C. and 1 atmospheric pressure, liquid water and a gaseous phase comprising at least 0.1% oxygen by volume, including but not limited to at least 0.5%, at least 1%, at least 2%, at least 5%, at least 8%, at least 10%, at least 12%, at least 15%, at least 18%, at least 20%, at least 25%, at least 30%, or at least 35% oxygen by volume. In some embodiments, the oxygen content of the gaseous phase of the first flushing medium is about 0.1% to about 30% by volume, such as about 0.5% to about 30%, about 1% to about 30%, about 1% to about 25%, about 1% to about 20%, or about 5% to about 20% by volume. In some embodiments, the oxygen content of the gaseous phase of the first flushing medium is about 5% to about 20% by volume. In some embodiments, the oxygen content of the gaseous phase of the first flushing medium is about 1%, about 5%, about 10%, about 15%, about 20%, or about 25% by volume. In some embodiments, the oxygen content of the gaseous phase of the first flushing medium is about 20% by volume. The gaseous phase of the first flushing medium can further comprise an inert gas. The inert gas can be, for example, nitrogen, argon, helium, neon, krypton, xenon, radon, carbon dioxide, or a combination thereof.

The gaseous phase of the first flushing medium can have a composition that is the same as or similar to air. In some embodiments, the first flushing medium comprises, measured at 25° C. and 1 atmospheric pressure, liquid water and a gaseous phase comprising at least 50% air by volume, including but not limited to at least 60%, at least 70%, at least 80%, at least 90%, at least 95%, at least 96%, at least 97%, at least 98%, or at least 99% air by volume. In some embodiments, the gaseous phase of the first flushing medium consists of air. As used herein, "air" refers to gases surrounding the earth, which may vary regionally, and are a function of various factors, such as temperature and pressure. As one example, the term "air" may refer to a gaseous composition composed, in a dry volume percentage (vol %), of about 78 vol % nitrogen, about 20.9 vol % oxygen, about 0.9 vol % argon, about 0.04 vol % carbon dioxide, and other elements and compounds such as helium, methane, krypton, hydrogen, nitrous oxide, xenon, ozone, carbon monoxide, sulfur dioxide, nitrogen dioxide, and ammonia. In this example, a gaseous phase comprising at least 50% air by volume would comprise at least 10% oxygen by volume. As nonlimiting examples, the gaseous phase of the first flushing medium can be air, a mixture of air and nitrogen, a mixture of air and oxygen, a mixture of oxygen and nitrogen, or a mixture of oxygen with one or more inert gases. The oxygen and nitrogen contents (net vol %) in some exemplary gaseous phases (made of the supplied gases) of the first flushing medium are as follows.

| Supplied Air | Supplied Nitrogen | Net Oxygen (approx.) | Net Nitrogen (approx.) |
|---|---|---|---|
| 5% | 95% | 1% | 99% |
| 10% | 90% | 2% | 98% |
| 50% | 50% | 10% | 90% |
| 75% | 25% | 15% | 85% |
| 100% | 0% | 20% | 80% |

| Supplied Air | Supplied Oxygen | Net Oxygen (approx.) | Net Nitrogen (approx.) |
|---|---|---|---|
| 95% | 5% | 24% | 76% |
| 90% | 10% | 28% | 72% |
| 80% | 20% | 36% | 64% |

| Supplied Oxygen | Supplied Nitrogen | Net Oxygen (approx.) | Net Nitrogen (approx.) |
|---|---|---|---|
| 1% | 99% | 1% | 99% |
| 20% | 80% | 20% | 80% |

The present method may include maintaining contact of the hydrogenation catalyst with the first flushing medium for an air-treatment duration to produce an air-treated catalyst. As used herein, the terms "air-treatment," "air-treated," "oxygen-treatment," "oxygen-treated," and the like, refer to a treatment with air or any other natural or artificial gaseous composition that includes oxygen. The air-treatment duration can be at least 30 minutes, including but not limited to at least 1 hour, at least 2 hours, at least 4 hours, at least 8 hours, at least 12 hours, or at least 24 hours. In some embodiments, the air-treatment duration is about 2 hours to about 8 hours, such as about 2 hours to about 4 hours.

In some embodiments, the second flushing medium comprises, measured at 25° C. and 1 atmospheric pressure, liquid water and a gaseous phase comprising at least 90% nitrogen by volume, including but not limited to at least 95%, at least 96%, at least 97%, at least 98%, or at least 99% nitrogen by volume. In some embodiments, the gaseous phase of the second flushing medium comprises at least 95% nitrogen by volume. In some embodiments, the gaseous phase of the second flushing medium comprises at least 99% nitrogen by volume. In some embodiments, the gaseous phase of the second flushing medium consists of nitrogen. In some embodiments, the gaseous phase of the second flushing medium is essentially free of oxygen. As used herein, the term "essentially free of oxygen" refers to less than 1%, or less than 0.5%, less than 0.1%, or less than 0.05% oxygen.

The gaseous phase of the second flushing medium can have a different composition from that of the gaseous phase of the first flushing medium. In particular, the gaseous phases of the first and second flushing medium can be different with respect to their oxygen content (e.g., in percent by volume). In some embodiments, the gaseous phase of the second flushing medium has an oxygen content that is less than the oxygen content of the gaseous phase of the first flushing medium. As a result, the catalyst can be exposed to a more oxidative atmosphere by contacting the first flushing medium, followed by exposure to a less oxidative or even inert atmosphere by contacting the second flushing medium. In particular embodiments, the gaseous phase of the first flushing medium comprises about 5% to about 20% oxygen by volume (e.g., air or similar gaseous composition having about 20% oxygen) and the gaseous phase of the second flushing medium is essentially free of oxygen (e.g., 99% or higher nitrogen).

The present method may include maintaining contact of the hydrogenation catalyst with the second flushing medium for a nitrogen-treatment duration to produce the regenerated hydrogenation catalyst. The nitrogen-treatment duration can be at least 30 minutes, including but not limited to at least 1 hour, at least 2 hours, at least 4 hours, at least 8 hours, at least 12 hours, at least 24 hours, or at least 48 hours. In some embodiments, the nitrogen-treatment duration is about 4 hours to about 24 hours, such as about 12 hours to about 24 hours. In some embodiments, the nitrogen-treatment duration is about 20 hours.

The air-treatment duration and the nitrogen-treatment duration in a given regeneration cycle can be adjusted and coordinated based on the other conditions of the regeneration cycle, such as temperature, pressure, and recycle rate of the flushing medium, in order to achieve desired regeneration results. For example, air-treatment duration can be 2-4 hours and the nitrogen-treatment duration can be about 20 hours in a regeneration cycle, in which the flushing medium is recycled at a recycle rate of 6-10 (such as a recycle rate of 8).

The contact of the first or the second flushing medium with the catalyst can be carried out, for example, by flowing the flushing medium across the surface of the catalyst. The contact can be maintained by controlling the flow rate of the flushing medium throughout the air-treatment duration and the nitrogen-treatment duration. As described herein, both the liquid and gaseous portion of the flushing medium can be recycled (as designed by the recycle rate described herein), and the present system can provide continuous flow of the recycled flushing medium to maintain the contact of the first or the second flushing medium with the catalyst. Typically, the contact of the gaseous component of the first flushing medium with the catalyst is stopped (e.g., switched off) before the contact of the gaseous component of the second flushing medium with the catalyst is started (e.g., switched on). When multiple regeneration cycles are performed, typically the contact of the second gaseous component of the flushing medium with the catalyst in the last cycle is stopped before the contact of the gaseous component of the first flushing medium with the catalyst in the next cycle is started. Thus, the present system allows for exposure of the catalyst to drastically different atmospheres (e.g., from primarily air to primarily nitrogen) in a single regenerating cycle or from one regeneration cycle to another regeneration cycle.

In some embodiments, the regeneration temperature is from 50° C. to 200° C. In some embodiments, the regeneration temperature is at least 50° C., or at least 60° C., or at least 70° C., or at least 80° C., or at least 90° C., or at least 100° C., or at least 110° C., or at least 120° C., or at least 130° C., to less than 140° C., or less than 150° C., or less than 160° C., or less than 170° C., or less than 180° C., or less than 190° C., or less than 200° C. In some embodiments, the regeneration cycle is performed at a temperature from about 70° C. to about 120° C. For example, step (a-i), step (a-ii), or both of the regeneration cycle can be performed at a temperature of about 70° C. to about 120° C.

In some embodiments, the regeneration pressure is from 20 psig to 300 psig. In some embodiments, the regeneration pressure is at least 20 psig, or at least 30 psig, or at least 40 psig, or at least 50 psig, or at least 60 psig, or at least 70 psig, or at least 80 psig, or at least 90 psig, or at least 100 psig, to less than 110 psig, or less than 125 psig, or less than 150 psig, or less than 200 psig, or less than 250 psig, or less than 300 psig. In some embodiments, the regeneration cycle is performed at a pressure from about 50 psig to about 200 psig. For example, step (a-i), step (a-ii), or both of the regeneration cycle can be performed at a pressure from about 50 psig to about 200 psig.

In some embodiments, the flow of the gaseous phase of the flushing medium to the reactor can be stopped while the liquid phase of the flushing medium is continued. The duration of the extra liquid flushing occurs for at least 30 minutes, or at least 1 hour, or at least 2 hours, or at least 3 hours, or at least 4 hours, or at least 5 hours, at least 6 hours, or less than 24 hours, or less than 2 days, or less than 3 days, or less than 4 days, or less than 5 days, or less than 6 days, or less than one week, or longer.

In some embodiments, the oxygen content in the flushing medium (e.g., the gaseous phase of the first flushing medium) is selected based on the amount of hydrogenation catalyst 38 in the reactor 12. In some embodiments, the first flushing medium comprises an oxygen to catalyst flux ratio ($O_2$/cat/hr) from $0.1*10^{-3}$ to $100*10^{-3}$ (mol/g/hr). In some embodiments, the $O_2$/cat/hr flux ratio is at least $0.1*10^{-3}$ (mol/g/hr), such as at least $0.5*10^{-3}$ (mol/g/hr), or at least $1*10^{-3}$ (mol/g/hr). In some embodiments, the $O_2$/cat/hr flux ratio is less than $100*10^{-3}$ (mol/g/hr), such as less than $50*10^{-3}$ (mol/g/hr), less than $10*10^{-3}$ (mol/g/hr), or less than $5*10^{-3}$ (mol/g/hr).

In some embodiments, the water content in the first flushing medium is based on the amount of hydrogenation catalyst 38 in the reactor 12. In some embodiments, the first flushing medium comprises a water to catalyst flux ratio ($H_2O$/cat/hr) from 1 to 100 (g/g/hr). In some embodiments, the $H_2O$/cat/hr ratio of the first flushing medium is at least 1 (g/g/hr), such as at least 2 (g/g/hr), at least 5 (g/g/hr), or at least 10 (g/g/hr). In some embodiments, the $H_2O$/cat/hr ratio of the first flushing medium is less than 100 (g/g/hr), such as less than 50 (g/g/hr), less than 20 (g/g/hr), or less than 10 (g/g/hr).

In some embodiments, the second flushing medium comprises a nitrogen to catalyst flux ratio ($N_2$/cat/hr) from $0.1*10^{-3}$ to $100*10^{-3}$ (mols/w/hr). In some embodiments, the $N_2$/cat/hr flux ratio is at least $0.1*10^{-3}$ (mol/g/hr), such as at least $0.5*10^{-3}$ (mol/g/hr), or at least $1*10^{-3}$ (mol/g/hr). In some embodiments, the $N_2$/cat/hr flux ratio is less than $100*10^{-3}$ (mol/g/hr), such as less than $50*10^{-3}$ (mol/g/hr), less than $10*10^{-3}$ (mol/g/hr), or less than $5*10^{-3}$ (mol/g/hr).

In some embodiments, the water content in the second flushing medium is based on the amount of hydrogenation catalyst 38 in the reactor 12. In some embodiments, the second flushing medium comprises a water to catalyst flux ratio ($H_2O$/cat/hr) from 1 to 100 (g/g/hr). In some embodiments, the $H_2O$/cat/hr ratio of the second flushing medium is at least 1 (g/g/hr), such as at least 2 (g/g/hr), at least 5

(g/g/hr), or at least 10 (g/g/hr). In some embodiments, the $H_2O$/cat/hr ratio of the second flushing medium is less than 100 (g/g/hr), such as less than 50 (g/g/hr), less than 20 (g/g/hr), or less than 10 (g/g/hr).

The nitrogen content in the gaseous phase of the second flushing medium may be selected to provide a desired inert atmosphere in contrast to the oxidative atmosphere caused by the gaseous phase of the first flushing medium (e.g., at least 90% air by volume). In some embodiments, the second flushing medium comprises, measured at 25° C. and 1 atmospheric pressure, a gaseous phase comprising at least 99% nitrogen by volume.

The inclusion of water in the flushing medium offers various advantages. First, water acts as a heat sink in the flushing medium that allows improved control over the temperature of the reactor 12 relative to a flushing medium composed solely of gases. This improved heat control avoids the creation of hot spots that may burn away catalytic supports, such as carbon. Water is also a polar solvent that may facilitate the removal of certain impurities, such as ionic salts and other polar moieties. In addition, the inclusion of water in the flushing medium allows the hydrogenation catalyst 38 to remain wetted during regeneration. Flushing media composed solely of gases can dry out the catalyst, which can create cracks in the fixed bed and lead to an increase in replacement frequency.

In some embodiments, the flushing medium is substantially free or entirely free of hydrogen peroxide. As used herein, the term "substantially free of hydrogen peroxide" refers to less than 1%, or less than 0.5%, or less than 0.1%, or less than 0.05% hydrogen peroxide. In some embodiments, the flushing medium is substantially free or entirely free of hydrogen peroxide prior to entering the reactor 12.

The effluents generated from the first the second flushing mediums are treated with ion exchange (IX) resin, and the IX-treated effluents are recycled back to the first and second flushing mediums. In some embodiments, the ion exchange resin is an anionic ion exchange resin. For example, the anionic ion exchange resin can have an amine or quaternary ammonium functional group. Commercially available anionic ion exchange resin or mixed bed resin includes those supplied by Purolite (PA, USA), such as UltraClean™ UCW3700 and Purolite® A100Plus. As nonlimiting examples, an ion exchange bed can be configured to receive the effluents from the reactor (FIG. 1B). The ion exchange bed can include a strong base (SB) anion resin or a weak base (WB) anion resin with different thermal stability profiles.

The treatment of the effluents by the ion exchange resin can be accomplished by known technique or according to the commercial supplier's instruction. In some embodiments, the effluents are treated by contacting the ion exchange resin at a temperature of about 20° C. to about 150° C. The ion exchange treatment temperature can be, for example, about 40° C. to about 120° C., about 60° C. to about 120° C., about 70° C. to about 120° C., or about 80° C. to about 120° C. The ion exchange treatment temperature can be about 20° C., about 40° C., about 60° C., about 80° C., about 100° C., or about 120° C. In some embodiments, the effluents are treated by contacting the ion exchange resin at a temperature of about 70° C. to about 120° C. As a nonlimiting example, a heat exchanger can be placed between the reactor and the ion-exchange bed to adjust the effluent's temperature prior to contacting the ion exchange resin bed.

In some embodiments, the effluents are treated by contacting the ion exchange resin at a pressure of about 0 psig to about 250 psig. The ion exchange treatment temperature can be, for example, about 0 psig to about 200 psig, about 0 psig to about 180 psig, about 0 psig to about 150 psig, or about 0 psig to about 100 psig. In some embodiments, the effluents are treated by contacting the ion exchange resin at a pressure of about 0 psig to about 200 psig.

In some embodiments, one or more the regeneration cycles are employed to produce the regenerated hydrogenation catalyst. For example, the method may include subjecting the fouled hydrogenation catalyst to one, two, three, four, or more regeneration cycles as described herein, and the conditions of one regeneration cycle (such as temperature, pressure, and duration) may be controlled independent of the corresponding conditions of another regeneration cycle. For example, a first regeneration cycle may be performed at a different temperature or a different pressure, or for a different duration than a second regeneration cycle.

Unlike typical catalyst regeneration processes, which operate in gas-phase conditions under temperatures in excess of 200° C. (e.g., decoking and desulphurization reactions), or utilize oxidants that degrade the catalyst's physical structure over time (e.g., $H_2O_2$-based regeneration), the present disclosure provides a method for regenerating a hydrogenation catalyst 38 with a flushing medium that operates under less severe conditions (e.g., temperatures of less than 200° C.). As reported in the co-pending U.S. patent application Ser. No. 17/891,093, a flushing medium comprising water, oxygen, and an inert/diluent gas at the specified regeneration pressures and temperatures is effective in restoring catalytic activity by removing impurities from the hydrogenation catalyst and maintaining the catalyst's structural integrity (e.g., total surface, pore size, pore volume). U.S. patent application Ser. No. 18/416,818 discloses that the regeneration efficiency can be further improved by switching the gaseous phase of the flushing medium from air (higher oxygen or oxidative atmosphere) to nitrogen (lower oxygen or inert atmosphere), as more impurities (such as sulfur-containing impurities) can be removed the fouled catalyst during the nitrogen-treatment duration. By adapting to atmospheric switching between different gaseous phases, fouled hydrogenation catalysts can be regenerated more efficiently at reduced cost. For example, the nitrogen-treatment duration can be adjusted according to the recycle rate of the flushing medium to reduce water consumption and improve removal of impurities (e.g., sulfur-containing impurities). Thus, a "pulsed" regeneration process having multiple regeneration cycles can be realized, each cycle undergoing a switch between an oxidative atmosphere (e.g., a pulse of air-treatment) and an inert atmosphere (e.g., a pulse of nitrogen-treatment), thus providing more flexibility and efficiency in controlling the regeneration process. The "pulsed" regeneration system can be more effective in removing sulfur from a fouled catalyst than a system not utilizing air/nitrogen switching, where the feedstock contains higher than normal sulfur-containing impurities.

The present system can be configured to accommodate both of the previous regeneration systems. Furthermore, the present system allows removal of impurities in the regeneration effluents (e.g., sulfate) and recycling of ion exchange-treated effluents, which have significantly reduced impurity levels, for re-use in the flushing medium. Advantageously, the present disclosure provides an effective system and method to regenerate hydrogenation catalyst with reduced water consumption and/or shortened overall regeneration time. The ion exchange resin bed can be replaced or regenerated off line in a cost-effective manner. Thus, the present system has superior capability over the previous systems in regenerating hydrogenation catalysts at reduced cost and with overall efficiency.

In another aspect, the present disclosure provides a method for producing a regenerated hydrogenation catalyst from a fouled hydrogenation catalyst, the method comprising:

catalytically reacting a feedstock stream having at least one sulfur-containing impurity in the presence of a hydrogenation catalyst to produce the fouled hydrogenation catalyst, wherein the fouled hydrogenation catalyst comprises an amount of sulfur derived from the at least one sulfur-containing impurity of the feedstock stream, and subjecting the fouled hydrogenation catalyst to a regeneration cycle to produce the regenerated hydrogenation catalyst, the regeneration cycle comprising:

(a-i) contacting the catalyst with a first flushing medium for an air-treatment duration to produce an air-treated catalyst and a first effluent, wherein the first flushing medium comprises, measured at 25° C. and 1 atmospheric pressure, liquid water and a gaseous phase comprising oxygen;

(b) contacting at least a portion of the first effluent with an anionic ion exchange resin to produce a first IX-treated effluent; and (c) recycling the first IX-treated effluent to step (a-i) for inclusion in the first flushing medium, wherein the amount of sulfur in the regenerated hydrogenation catalyst is reduced relative to the fouled hydrogenation catalyst.

In some embodiments, the regeneration cycle further comprises:

(a-ii) contacting the air-treated catalyst with a second flushing medium for a nitrogen-treatment duration to produce a nitrogen-treated catalyst and a second effluent, wherein the second flushing medium comprises, measured at 25° C. and 1 atmospheric pressure, liquid water and a gaseous phase comprising at least 90% nitrogen by volume;

(b) contacting at least a portion of the first effluent and at least a portion of the second effluent with the ion exchange resin to produce the first IX-treated effluent and a second IX-treated effluent, respectively, and (c) recycling the first IX-treated effluent and the second IX-treated effluent to steps (a-i) and (a-ii) for inclusion in the first flushing medium and the second flushing medium, respectively.

The fouled hydrogenation catalyst can be, for example, a hydrogenation catalyst that has been exposed to a feedstock solution under the specified hydrogenation conditions (e.g., temperatures, pressures, concentrations of feedstock) described herein for a period of time (e.g., at least 1 day, at least 2 days, at least 3 days, at least 4 days, at least 5 days, at least 6 days, at least one week, at least two weeks, at least three weeks, at least one month, at least six months, at least one year). The fouled hydrogenation catalyst can be produced by exposing a fresh catalyst that has never been exposed to the feedstock solution at the specified hydrogenation conditions, or by exposing a freshly regenerated catalyst to the specified hydrogenation conditions.

Suitable first and second flushing media include those described above. In some embodiments, the gaseous phase of the first flushing medium comprises about 0.1% to about 30% oxygen by volume. The gaseous phase of the first flushing medium can further comprise an inert gas, such as nitrogen, argon, helium, neon, krypton, xenon, radon, carbon dioxide, or a combination thereof. In some embodiments, the gaseous phase of the first flushing medium comprises at least 90% air by volume. In some embodiments, the gaseous phase of the second flushing medium comprises at least 99% nitrogen by volume. In some embodiments, the gaseous phase of the second flushing medium is essentially free of oxygen. In some embodiment, the method comprises subjecting the nitrogen-treated catalyst to a successive set of the operations (a) and (b) of the regeneration cycle, each with a respective treatment duration, to produce the regenerated hydrogenation catalyst. For example, the method may include subjecting the nitrogen-treated catalyst to one, two, three, four, or more successive regeneration cycles as described herein. Advantageously, the conditions of each of the regeneration cycles (such as temperature, pressure, and duration) may be independently controlled. Also, the air-treatment duration and the nitrogen-treatment duration in each regeneration cycle can be coordinated to improve regeneration efficiency, based on the sulfur content in the feedstock, the amount of sulfur in the fouled catalyst, and recycle rate of the flushing medium.

In some embodiments, the air-treatment duration in one or more of the regeneration cycles is at least 30 minutes, such as about 2-4 hours.

In some embodiments, the nitrogen-treatment duration in one or more of the regeneration cycles is at least 30 minutes or at least 4 hours, such as at about 12-24 hours.

In some embodiments, the amount of sulfur in the nitrogen-treated hydrogenation catalyst or the regenerated hydrogenation catalyst is reduced by at least 5% relative to the fouled hydrogenation catalyst. The reduction can be at least a 10% reduction, at least a 15% reduction, at least a 20% reduction, at least a 30% reduction, at least a 40% reduction, at least a 50% reduction, or at least a 60% reduction relative to the sulfur content of the fouled hydrogenation catalyst.

In some embodiments, the air-treatment duration is at least 30 minutes, the nitrogen-treatment duration is at least 4 hours, and the amount of sulfur in the regenerated hydrogenation catalyst is reduced by at least 5% relative to the fouled hydrogenation catalyst. In some embodiments, multiple regeneration cycles (e.g., a total of two, three, four, five, six, seven, eight, night, or ten cycles) are performed in the present method, wherein at least one of the cycles includes an air-treatment duration of at least 30 minutes and an nitrogen-treatment duration of at least 4 hours, and wherein the amount of sulfur in the regenerated hydrogenation catalyst is reduced by at least 5% relative to the fouled hydrogenation catalyst.

In some embodiments, steps (a-i) and (a-ii) of the regeneration cycle are performed at a temperature from about 70° C. to about 120° C. In some embodiments, step (b) of the regeneration cycle is performed at a temperature from about 20° C. to about 120° C. In some embodiments, steps (a-i), (a-ii), and (b) of the regeneration cycle is performed at a temperature from about 70° C. to about 120° C. In some embodiments, multiple regeneration cycles (e.g., a total of two, three, four, five, six, seven, eight, night, or ten cycles) are performed in the present method and at least one of the multiple regeneration cycles is performed at a temperature from about 70° C. to about 120° C.

In some embodiments, steps (a-i) and (a-ii) of the regeneration cycle are performed at a pressure from about 50 psig to about 200 psig. In some embodiments, step (b) of the regeneration cycle is performed at a pressure from about 0 psig to about 200 psig. In some embodiments, steps (a-i), (a-ii), and (b) of the regeneration cycle are performed at a pressure from about 50 psig to about 200 psig. In some embodiments, multiple regeneration cycles (e.g., a total of two, three, four, five, six, seven, eight, night, or ten cycles) are performed in the present method and at least one of the multiple regeneration cycles is performed at a pressure from about 50 psig to about 200 psig.

In some embodiments, the method includes subjecting the fouled hydrogenation catalyst to multiple regeneration cycles, each cycle independently comprising: step (a-i), (b), and (c); or steps (a-i), (a-ii), (b) and (c) to produce the regenerated hydrogenation catalyst. In some embodiments, at least one of the multiple regeneration cycles comprises steps (a-i), (a-ii), (b), and (c). For example, the method can include subjecting the fouled hydrogenation catalyst to a total of five regeneration cycles, in which the first cycle includes step (a-i), (b), and (c) and the subsequent four cycles includes steps (a-i), (a-ii), (b) and (c). The sequence of different regeneration cycles, as well as the conditions for each individual regeneration cycle, can be adjusted according to the specific conditions of the feed stock, the type of the catalyst, and the desired water consumption level and regeneration time.

The present method can be particularly effective in in regenerating catalysts used for hydrogenating feedstock with a higher than normal level of sulfur-containing impurities. In some embodiments, the feedstock stream has an amount of sulfur of at least 0.1 ppm, including but not limited to at least 0.2 ppm, at least 0.3 ppm, at least 0.4 ppm, at least 0.5 ppm, at least 1.0 ppm, at least 2.0 ppm, at least 5.0 ppm, at least 10.0 ppm, at least 20 ppm, at least 30 ppm, at least 40 ppm, at least 50 ppm, and at least 100 ppm. In some embodiments, the feedstock stream has an amount of sulfur of at least 0.5 ppm, such as at least 1.0 ppm or at least 5 ppm.

In some embodiments, the amount of sulfur removed from the catalyst is measured to monitor the progress of the regeneration process. Based on this information, the conditions for further regeneration cycles (such as temperature, pressure, air-treatment duration, and nitrogen-treatment duration) can be adjusted to improve efficiency. In some embodiments, the present method further comprises: measuring a first sulfur content of the first flushing medium after contacting the catalyst in (a) and/or measuring a second sulfur content of the second flushing medium after contacting the catalyst in (b); and subjecting the nitrogen-treated catalyst to a successive set of the operations (a) and (b), each with a respective treatment duration. The sulfur content in the flushing medium can be measured by any suitable analytic method. For example, the sulfur content can be measured by measuring conductivity and/or pH of the first flushing medium or the second flushing medium or by inductively coupled plasma (ICP) methods.

In some embodiments, the regenerated hydrogenation catalysts exhibit excellent retention in catalytic activity after regenerative treatment. As used herein, the term "retain," "retaining," or "retention," with respect to a reference value, includes both partial and increased values relative to the reference value. For example, a specified parameter (e.g., conversion of a regenerated catalyst) can retain less than 100% or more than 100% of a reference parameter (e.g., conversion of a fresh catalyst or a fouled catalyst from which the regenerated catalyst is produced).

Typically, the fouled catalyst has lower catalytic capacity (e.g., as measured by the conversion value) than the fresh catalyst. The catalytic capacity of a fouled catalyst may be increased by the regeneration method as described herein to a level close to that of the fresh (or freshly regenerated) catalyst from which the fouled catalyst is produced. That is, the regeneration method herein may be used to retore the catalytic capacity of a fouled catalyst back to the level of the fresh (or freshly regenerated) catalyst. The conversion value as describe herein (as a measurement of catalytic capacity) of a regenerated catalyst, or the conversion value of a fouled catalyst from which the regenerated catalyst is produced, may be compared to that of a fresh catalyst. For example, the conversion value of a fouled catalyst may be about 50%, about 60%, about 70%, about 80%, or about 90% of the conversion value of a fresh catalyst. For example, the conversion value of a regenerated catalyst may be about 70%, about 80%, about 90%, about 95%, about 99%, about 100%, or about 110% the catalytic capacity of a fresh catalyst. In some embodiments, the conversion value of a regenerated catalyst is at least 5%, at least 10%, at least 20%, at least 50%, at least 70%, at least 90%, or at least 100% higher than that of a fouled catalyst. In some embodiments, regenerated catalyst retains at least 100%, at least 105%, at least 110%, at least 120%, at least 150%, at least 170%, at least 190%, or at least 200% of the conversion value of a fouled catalyst. As an example, the conversion value of a fresh catalyst is 0.96 and the conversion value of a fouled catalyst is 0.70 (or 73% of the fresh catalyst). After regeneration, the conversion value of the regenerated catalyst is 0.94 (or 98% of the fresh catalyst). In this example, the regenerated catalyst retains 134% of the conversion of the fouled catalyst (or the conversion value of a regenerated catalyst is 34% higher than that of the fouled catalyst).

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms. As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter. As used herein, the singular forms "a", "an", and "the" include plural embodiments unless the context clearly dictates otherwise. The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1.

The present invention has been described in terms of one or more preferred embodiments, and it should be appreciated that many equivalents, alternatives, variations, and modifications, aside from those expressly stated, are possible and within the scope of the invention.

EXAMPLES

Example 1

In a preliminary study, an effluent sample from a WAOR process with a conductivity of ~200 uS/cm was introduced to a mixed bed ion exchange (IX) resin, and the conductivity of the sample after IX treatment was reduced to <10 uS/cm, demonstrating the ability of IX resin to remove sulfate from solution.

Figure 2:
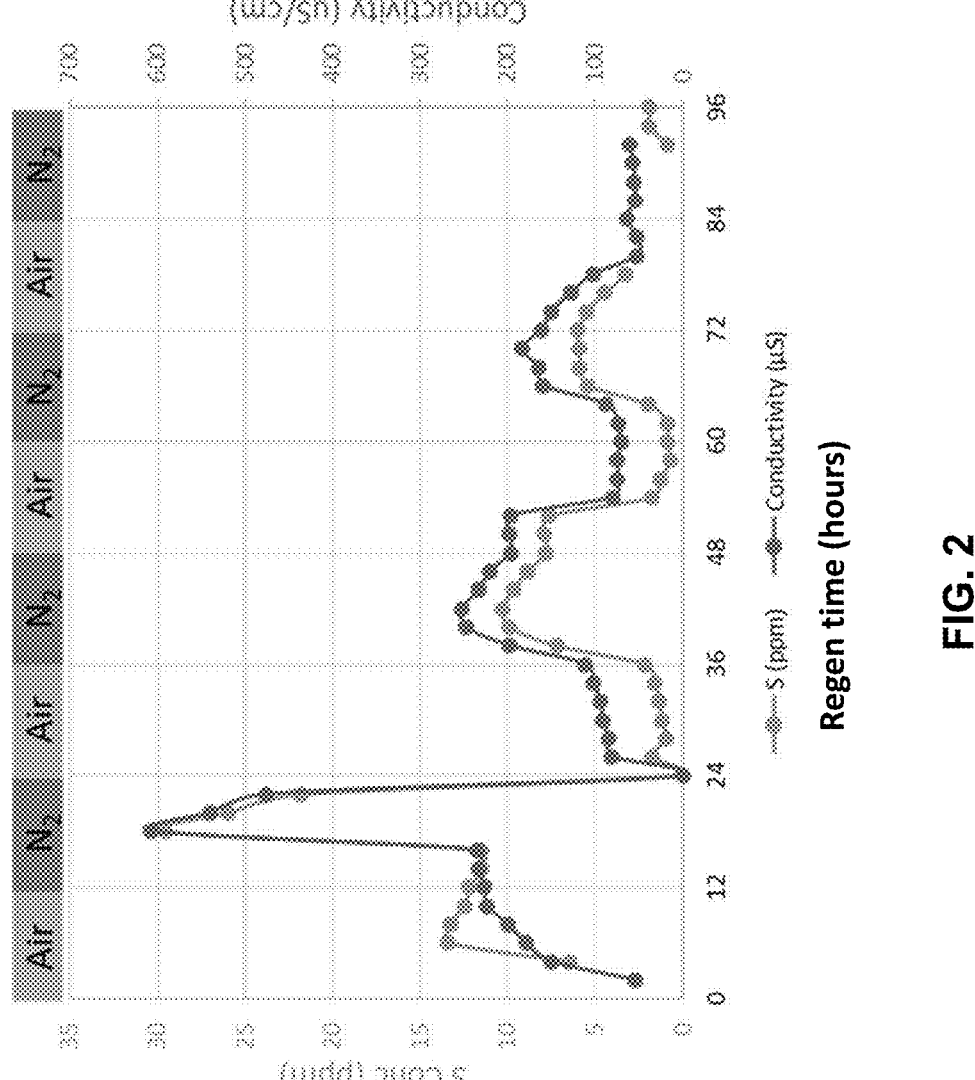
FIG. 2 shows representative results of the sulfur content and the conductivity of the aqueous effluent from a pulsed regeneration using a 6:1 aqueous recycle ratio in a WAOR process.
Figure 3:
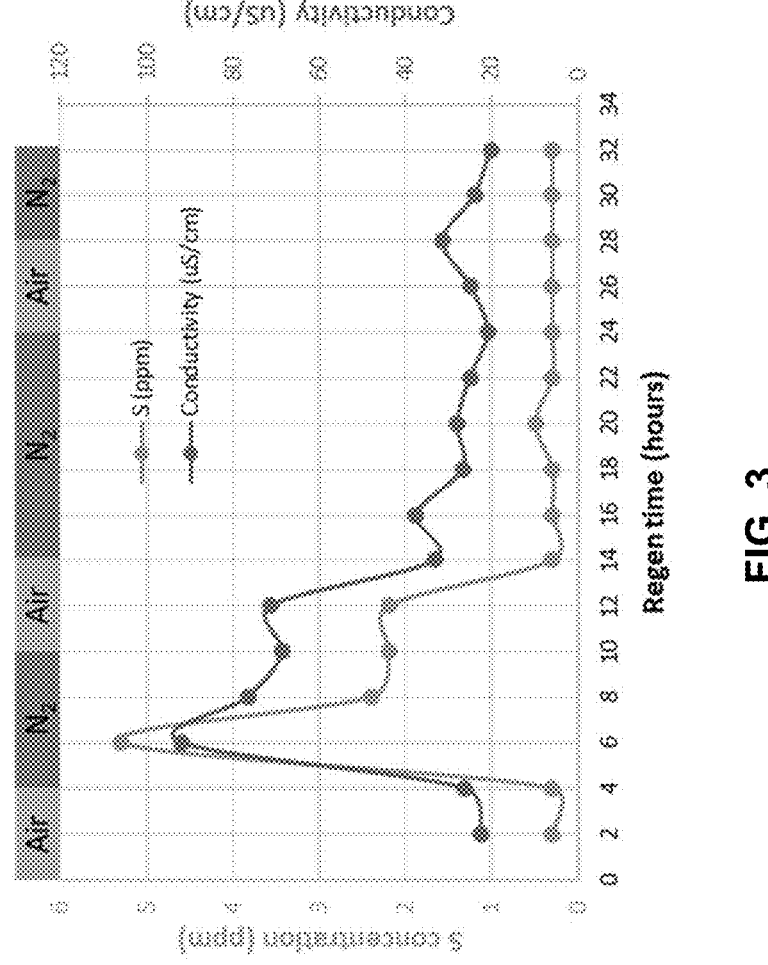
FIG. 3 shows representative results of the sulfur content and the conductivity of the aqueous effluent from a pulsed regeneration without an aqueous recycle.

The advantages of the present process over the previous studies can be shown by comparing the pulsed regenerations in FIG. 2 and FIG. 3. Typically, fresh Ru/C hydrogenation catalysts were deactivated by hydrogenating corn syrup feeds. The hydrogenation reactions were operated on stream for multiple weeks until the hydrogenation catalysts were sufficiently deactivated. Various WAOR experiments were performed on deactivated hydrogenation catalysts. Conditions for a standard WAOR process were as follows: 100% air flow, 100-110° C. inlet temperature, 100 psig reactor pressure, with water and air flowed for 24 hours. After 24 hours, water flow continued but the system was purged with $N_2$ to remove any traces of oxygen before hydrogen was introduced to reduce the catalyst. For a pulsed WAOR process, 100% air flow (e.g., at 110° C. and 100 psig) and $N_2$ flow (e.g., at 110° C. and 100 psig) were each performed for designated time periods (e.g., 4 hours to 24 hours).

In FIG. 2, a 6:1 recycle/fresh water ratio was used (36 kg/hr recycle flow to 6 kg/hr fresh water flow) and an air flow rate of 0.25 kg air/hr. This high recycle rate caused the conductivity readings and S concentration to be quite high (>600 uS/cm and 30 ppm during the first pulse, respectively) and 24 hours were needed for each air/$N_2$ cycle. Conversely, the regeneration in FIG. 3 did not have an aqueous recycle and instead ran at a fresh water rate of 42 kg/hr and the same air rate (0.25 kg/hr). With no recycle, the max conductivity was approximately 90 uS/cm and max sulfur concentration was around 5 ppm, each value being about 6× lower than when using a 6:1 recycle ratio. More importantly, each air/$N_2$ pulse only took 10-14 hours, shortening the overall regen time by over 2-fold. However, significantly more fresh water was needed for this regeneration.

Example 2

Figure 4:
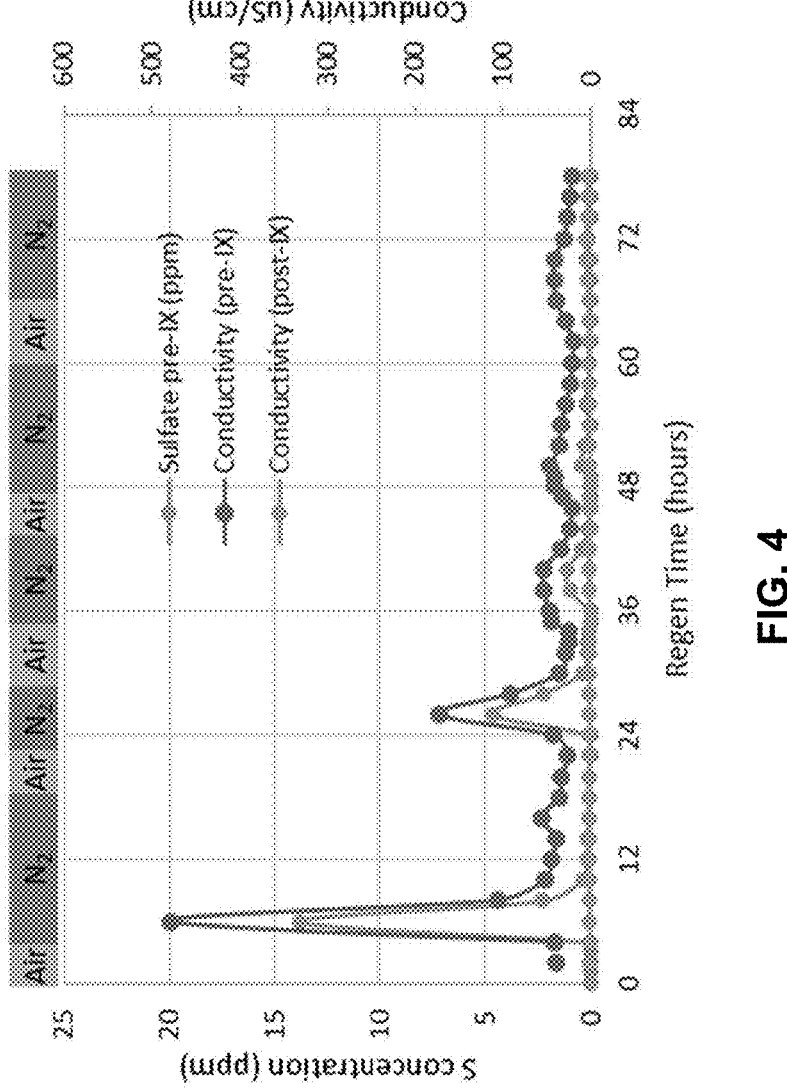
FIG. 4 shows sulfate content (pre-IX) and conductivity (both pre- and post-IX bed) for a pulsed regeneration process with a high recycle rate.

A WAOR was conducted after installing an IX bed in-line with the recycle stream. An upstream and downstream sample port were included to be able to obtain liquid samples for off-stream analysis. For this test, a 13:1 recycle rate and an air flow rate of 0.34 kg/hr were used. A mixed bed ion exchange resin (Purolite UCW3700) was loaded into a 3" OD×48" long stainless steel pipe (FIG. 1B). The IX bed was maintained at ambient conditions (0 psig and room temperature). Five total air/$N_2$ pulses were performed (FIG. 4), and comparison of the conductivity pre- and post-IX bed showed the bed was very effective at removing ions, as shown by a pre-IX bed conductivity of 500 uS/cm being decreased to <5 uS/cm post-IX bed. Based on the post-IX conductivity, the pulse lengths may be decreased.

In addition to operating the IX bed at ambient conditions, there are situations where it may be advantageous to operate the IX bed at the regen conditions (for instance, 100° C. and 100 psig). These conditions may be outside those specified by various resin suppliers. To test the stability of a weak base anion exchange resin (WBA) under these conditions, breakthrough curves were collected using a model feed composed of dilute sulfuric acid. In the model study, the species that needs to be removed during the WAOR process is sulfate, in the form of sulfuric acid. A ½" OD reactor was loaded with 25 g of Purolite® A100Plus resin (at a density of ~0.67 g/mL, corresponding to roughly 0.038 L) and a model WAOR recycle stream was made by diluting sulfuric acid in DI water to a concentration of 70 ppm. The reactor was heated to 100° C. and set to an outlet pressure of 100 psig. The model sulfuric acid feed was flowed at a rate of 10 bed volumes per hour (10 BV/hr, or 6.5 mL/min). After each cycle, the resin was unloaded and regenerated with a 4% NaOH solution at a rate of 2.4 BV/hr (1.5 mL/min) for one hour.

Figure 5:
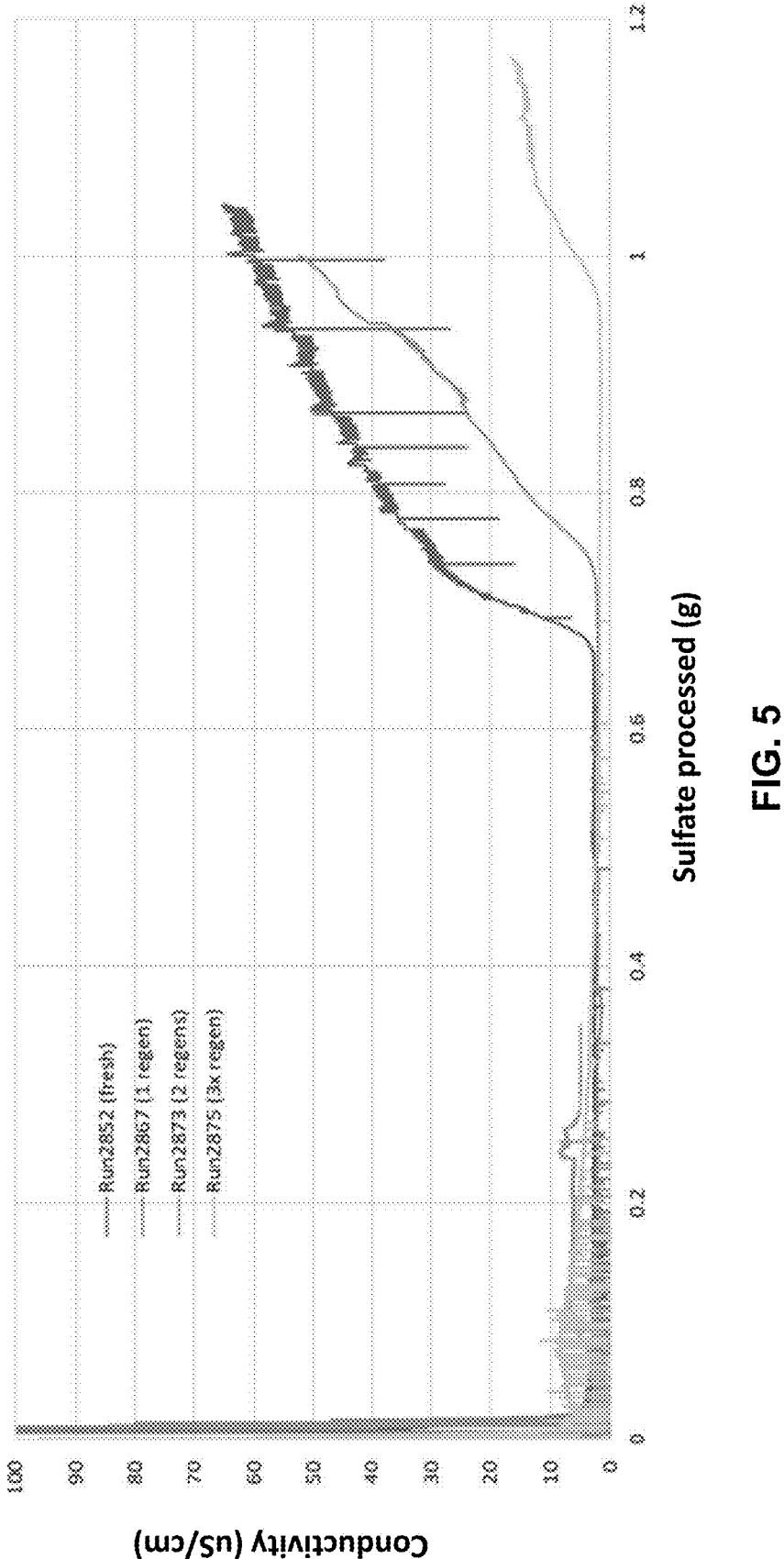
FIG. 5 shows results of in-line conductivity measurement as a function of sulfate processed through weak base anion exchange resin. The test conditions were: 70 ppm sulfuric acid in water (except for Run2873, which used 10 ppm), 100° C., 100 psig, and 10 BV/hr flow rate.

Four ion exchange cycles were tested to test the capacity of the resin bed, as measured by sulfate processed (g) before breakthrough (turning point of conductivity increase, see FIG. 5). In the first cycle (Run2852), with fresh resin, 0.67 g of sulfate was processed before a breakthrough in conductivity was observed. The resin was regenerated, and on the second cycle (Run2867) the resin displayed a higher sulfate capacity, processing 0.75 g before conductivity breakthrough. The resin was regenerated a second time, but a lower sulfuric acid concentration was used for this test (approximately 10 ppm, Run2873), so no conductivity breakthrough occurred. After a third and final regeneration, the resin displayed an even greater sulfate capacity, processing nearly 1 g of sulfate before conductivity breakthrough (nearing 26.6 g sulfate/L resin, Run2875). The source of this increased capacity is unclear, and these results are unexpected. Overall, these results showed that a WBA resin is capable of removing sulfate from a simulated WAOR recycle stream under process-relevant conditions (100° C. and 100 psig). The sulfate capacity of the resin increased with regeneration number, which is a surprising result. The resin capacity can range about 18-26 g sulfate per L of resin.

Overall, various experiments were conducted with the IX bed at either ambient conditions (e.g., during actual WAOR process a with mixed bed resin) or elevated temperature and pressure (e.g., using a model WAOR recycle stream). These results demonstrated the effectiveness of an in-line IX bed on removing sulfate from the WAOR recycle stream.

For reasons of completeness, various aspects of the invention are set out in the following numbered clauses:

Clause 1. A method for hydrogenating biomass, the method comprising:

catalytically reacting a feedstock stream comprising water and an oxygenated hydrocarbon ($C_{2+}O_{1+}$) with hydrogen in the presence of a hydrogenation catalyst for a hydrogenation duration to produce a first hydrogenated product stream and a fouled hydrogenation catalyst;

subjecting the fouled hydrogenation catalyst to a regeneration cycle to produce a regenerated hydrogenation catalyst, the regeneration cycle comprising:

(a-i) contacting the catalyst with a first flushing medium for an air-treatment duration to produce an air-treated catalyst and a first effluent, wherein the first flushing medium comprises, measured at 25° C. and 1 atmospheric pressure, liquid water and a gaseous phase comprising oxygen;

(b) contacting at least a portion of the first effluent with an ion exchange resin to produce a first IX-treated effluent; and (c) recycling the first IX-treated effluent to step (a-i) for inclusion in the first flushing medium, and catalytically reacting the feedstock stream with hydrogen in the presence of the regenerated hydrogenation catalyst to further produce a second hydrogenated product stream.

Clause 2. The method of clause 1, wherein the regeneration cycle further comprises:

(a-ii) contacting the air-treated catalyst with a second flushing medium for a nitrogen-treatment duration to produce a nitrogen-treated catalyst and a second effluent, wherein the second flushing medium comprises, measured at 25° C. and 1 atmospheric pressure, liquid water and a gaseous phase comprising at least 90% nitrogen by volume;

(b) contacting at least a portion of the first effluent and at least a portion of the second effluent with the ion exchange resin to produce the first IX-treated effluent and a second IX-treated effluent, respectively, and (c) recycling the first IX-treated effluent and the second IX-treated effluent to steps (a-i) and (a-ii) for inclusion in the first flushing medium and the second flushing medium, respectively.

Clause 3. The method of any one of clauses 1-2, wherein the air-treatment duration is at least 30 minutes.

Clause 4. The method of any one of clauses 1-3, wherein the nitrogen-treatment duration is at least 30 minutes.

Clause 5. The method of any one of clauses 1-4, wherein step (a-i), step (a-ii), or both of the regeneration cycle is performed at a temperature of about 70° C. to about 120° C.

Clause 6. The method of any one of clauses 1-5, wherein step (a-i), step (a-ii), or both of regeneration cycle is performed at a pressure of about 50 psig to about 200 psig.

Clause 7. The method of any one of clauses 1-6, wherein the first flushing medium comprises an oxygen to catalyst flux ratio ($O_2$/cat/hr) from $0.1*10^{-3}$ to $100*10^{-3}$ (mols/g/hr).

Clause 8. The method of any one of clauses 1-7, wherein the first flushing medium and/or the second flushing medium comprise a water to catalyst flux ratio ($H_2O$/cat/hr) from 1 to 100 (g/g/hr).

Clause 9. The method of any one of clauses 1-8, wherein the second flushing medium comprises a nitrogen to catalyst flux ratio ($N_2$/cat/hr) from $0.1*10^{-3}$ to $100*10^{-3}$ (mols/g/hr).

Clause 10. The method of any one of clauses 1-9, wherein the gaseous phase of the first flushing medium comprises about 0.1% to about 30% oxygen by volume.

Clause 11. The method of any one of clauses 1-10, wherein the gaseous phase of the first flushing medium further comprises an inert gas selected from the group consisting of nitrogen, argon, helium, neon, krypton, xenon, radon, carbon dioxide, and a combination thereof.

Clause 12. The method of any one of clauses 1-11, wherein the gaseous phase of the first flushing medium comprises at least 90% air by volume.

Clause 13. The method of any one of clauses 1-12, wherein the gaseous phase of the second flushing medium comprises at least 99% nitrogen by volume.

Clause 14. The method of any one of clauses 1-13, wherein the gaseous phase of the second flushing medium is essentially free of oxygen.

Clause 15. The method of any one of clauses 1-14, wherein the oxygenated hydrocarbon is a saccharide.

Clause 16. The method of any one of clauses 1-15, wherein the hydrogenation catalyst comprises a support and an active metal.

Clause 17. The method of clause 16, wherein the hydrogenation catalyst is ruthenium on carbon (Ru/C).

Clause 18. The method of any one of clauses 1-17, wherein the ion exchange resin is an anionic ion exchange resin.

Clause 19. The method of any one of clauses 1-18, wherein step (b) is carried out at a temperature of about 70° C. to about 120° C.

Clause 20. The method of any one of clauses 1-20, wherein step (b) is carried out at a pressure of about 0 psig to about 200 psig.

Clause 21. A method for producing a regenerated hydrogenation catalyst from a fouled hydrogenation catalyst, the method comprising:

catalytically catalyst to produce the fouled hydrogenation catalyst, wherein the fouled hydrogenation reacting a feedstock stream having at least one sulfur-containing impurity in the presence of a hydrogenation catalyst comprises an amount of sulfur derived from the at least one sulfur-containing impurity of the feedstock stream, and subjecting the fouled hydrogenation catalyst to a regeneration cycle to produce the regenerated hydrogenation catalyst, the regeneration cycle comprising:

(a-i) contacting the catalyst with a first flushing medium for an air-treatment duration to produce an air-treated catalyst and a first effluent, wherein the first flushing medium comprises, measured at 25° C. and 1 atmospheric pressure, liquid water and a gaseous phase comprising oxygen;

(b) contacting at least a portion of the first effluent with an anionic ion exchange resin to produce a first IX-treated effluent; and (c) recycling the first IX-treated effluent to step (a-i) for inclusion in the first flushing medium, wherein the amount of sulfur in the regenerated hydrogenation catalyst is reduced relative to the fouled hydrogenation catalyst.

Clause 22. The method of clause 21, wherein the regeneration cycle further comprises:

(a-ii) contacting the air-treated catalyst with a second flushing medium for a nitrogen-treatment duration to produce a nitrogen-treated catalyst and a second effluent, wherein the second flushing medium comprises, measured at 25° C. and 1 atmospheric pressure, liquid water and a gaseous phase comprising at least 90% nitrogen by volume;

(b) contacting at least a portion of the first effluent and at least a portion of the second effluent with the ion exchange resin to produce the first IX-treated effluent and a second IX-treated effluent, respectively, and (c) recycling the first IX-treated effluent and the second IX-treated effluent to steps (a-i) and (a-ii) for inclusion in the first flushing medium or the second flushing medium, respectively.

Clause 23. The method of any one of clauses 21-22, comprising subjecting the fouled hydrogenation catalyst to multiple regeneration cycles, each cycle independently comprising:

steps (a-i), (b), and (c); or steps (a-i), (a-ii), (b) and (c), to produce the regenerated hydrogenation catalyst.

Clause 24. The method of clause 23, wherein at least one of the multiple regeneration cycles comprises steps (a-i), (a-ii), (b), and (c).

The invention claimed is:

1. A method for hydrogenating biomass, the method comprising:

catalytically reacting a feedstock stream comprising water and an oxygenated hydrocarbon ($C_{2+}O_{1+}$) with hydrogen in the presence of a hydrogenation catalyst for a hydrogenation duration to produce a first hydrogenated product stream and a fouled hydrogenation catalyst;

subjecting the fouled hydrogenation catalyst to a regeneration cycle to produce a regenerated hydrogenation catalyst, the regeneration cycle comprising:

(a-i) contacting the catalyst with a first flushing medium for an air-treatment duration to produce an air-treated catalyst and a first effluent, wherein the first flushing medium comprises, measured at 25° C. and 1 atmospheric pressure, liquid water and a gaseous phase comprising oxygen;

(b) contacting at least a portion of the first effluent with an ion exchange resin to produce a first IX-treated effluent; and (c) recycling the first IX-treated effluent to step (a-i) for inclusion in the first flushing medium, and catalytically reacting the feedstock stream with hydrogen in the presence of the regenerated hydrogenation catalyst to further produce a second hydrogenated product stream.

2. The method of claim 1, wherein the regeneration cycle further comprises:

(a-ii) contacting the air-treated catalyst with a second flushing medium for a nitrogen-treatment duration to produce a nitrogen-treated catalyst and a second effluent, wherein the second flushing medium comprises, measured at 25° C. and 1 atmospheric pressure, liquid water and a gaseous phase comprising at least 90% nitrogen by volume;

(b) contacting at least a portion of the first effluent and at least a portion of the second effluent with the ion exchange resin to produce the first IX-treated effluent and a second IX-treated effluent, respectively, and (c) recycling the first IX-treated effluent and the second IX-treated effluent to steps (a-i) and (a-ii) for inclusion in the first flushing medium and the second flushing medium, respectively.

3. The method of claim 1, wherein the air-treatment duration is at least 30 minutes.

4. The method of claim 1, wherein the nitrogen-treatment duration is at least 30 minutes.

5. The method of claim 1, wherein step (a-i), step (a-ii), or both of the regeneration cycle is performed at a temperature of about 70° C. to about 120° C.

6. The method of claim 1, wherein step (a-i), step (a-ii), or both of regeneration cycle is performed at a pressure of about 50 psig to about 200 psig.

7. The method of claim 1, wherein the first flushing medium comprises an oxygen to catalyst flux ratio ($O_2$/cat/hr) from $0.1*10^{-3}$ to $100*10^{-3}$ (mols/g/hr).

8. The method of claim 1, wherein the first flushing medium and/or the second flushing medium comprise a water to catalyst flux ratio ($H_2O$/cat/hr) from 1 to 100 (g/g/hr).

9. The method of claim 1, wherein the second flushing medium comprises a nitrogen to catalyst flux ratio ($N_2$/cat/hr) from $0.1*10^{-3}$ to $100*10^{-3}$ (mols/g/hr).

10. The method of claim 1, wherein the gaseous phase of the first flushing medium comprises about 0.1% to about 30% oxygen by volume.

11. The method of claim 1, wherein the gaseous phase of the first flushing medium further comprises an inert gas selected from the group consisting of nitrogen, argon, helium, neon, krypton, xenon, radon, carbon dioxide, and a combination thereof.

12. The method of claim 1, wherein the gaseous phase of the first flushing medium comprises at least 90% air by volume.

13. The method of claim 1, wherein the oxygenated hydrocarbon is a saccharide.

14. The method of claim 1, wherein the hydrogenation catalyst comprises a support and an active metal.

15. The method of claim 14, wherein the hydrogenation catalyst is ruthenium on carbon (Ru/C).

16. The method of claim 1, wherein the ion exchange resin is an anionic ion exchange resin.

17. The method of claim 1, wherein step (b) is carried out at a temperature of about 70° C. to about 120° C.

18. The method of claim 1, wherein step (b) is carried out at a pressure of about 0 psig to about 200 psig.

19. A method for producing a regenerated hydrogenation catalyst from a fouled hydrogenation catalyst, the method comprising:

catalytically reacting a feedstock stream having at least one sulfur-containing impurity in the presence of a hydrogenation catalyst to produce the fouled hydrogenation catalyst, wherein the fouled hydrogenation catalyst comprises an amount of sulfur derived from the at least one sulfur-containing impurity of the feedstock stream, and subjecting the fouled hydrogenation catalyst to a regeneration cycle to produce the regenerated hydrogenation catalyst, the regeneration cycle comprising:

(a-i) contacting the catalyst with a first flushing medium for an air-treatment duration to produce an air-treated catalyst and a first effluent, wherein the first flushing medium comprises, measured at 25° C. and 1 atmospheric pressure, liquid water and a gaseous phase comprising oxygen;

(b) contacting at least a portion of the first effluent with an anionic ion exchange resin to produce a first IX-treated effluent; and (c) recycling the first IX-treated effluent to step (a-i) for inclusion in the first flushing medium, wherein the amount of sulfur in the regenerated hydrogenation catalyst is reduced relative to the fouled hydrogenation catalyst.

20. The method of claim 19, wherein the regeneration cycle further comprises:

(a-ii) contacting the air-treated catalyst with a second flushing medium for a nitrogen-treatment duration to produce a nitrogen-treated catalyst and a second effluent, wherein the second flushing medium comprises, measured at 25° C. and 1 atmospheric pressure, liquid water and a gaseous phase comprising at least 90% nitrogen by volume;

(b) contacting at least a portion of the first effluent and at least a portion of the second effluent with the ion exchange resin to produce the first IX-treated effluent and a second IX-treated effluent, respectively, and (c) recycling the first IX-treated effluent and the second IX-treated effluent to steps (a-i) and (a-ii) for inclusion in the first flushing medium and the second flushing medium, respectively.

* * * * *